(12) United States Patent
Strohm et al.

(10) Patent No.: US 10,175,158 B2
(45) Date of Patent: Jan. 8, 2019

(54) METHOD, SYSTEM AND APPARATUS FOR THE DETECTION, CHARACTERIZATION AND CLASSIFICATION OF PARTICLES USING PHOTOACOUSTIC AND ULTRASOUND TECHNIQUES

(71) Applicant: RYERSON UNIVERSITY, Toronto, Ontario (CA)

(72) Inventors: Eric Strohm, Mississauga (CA); Michael Kolios, Toronto (CA)

(*) Notice: Subject to any disclaimer, the term of this patent is extended or adjusted under 35 U.S.C. 154(b) by 109 days.

(21) Appl. No.: 14/425,361

(22) PCT Filed: Mar. 11, 2013

(86) PCT No.: PCT/CA2013/000212
§ 371 (c)(1),
(2) Date: Mar. 3, 2015

(87) PCT Pub. No.: WO2014/036630
PCT Pub. Date: Mar. 13, 2014

(65) Prior Publication Data
US 2015/0233811 A1    Aug. 20, 2015

Related U.S. Application Data

(60) Provisional application No. 61/696,455, filed on Sep. 4, 2012.

(51) Int. Cl.
*G01N 29/24* (2006.01)
*G01N 15/10* (2006.01)
(Continued)

(52) U.S. Cl.
CPC ......... *G01N 15/10* (2013.01); *G01N 29/2418* (2013.01); *G01N 29/46* (2013.01);
(Continued)

(58) Field of Classification Search
CPC .... G01N 15/10; G01N 29/46; G01N 29/2418; G01N 29/2425; G01N 2291/015;
(Continued)

(56) References Cited

U.S. PATENT DOCUMENTS

| 6,694,799 B2 | 2/2004 | Small |
| 7,665,364 B2 * | 2/2010 | Su ..................... G01N 29/0681 73/601 |

(Continued)

OTHER PUBLICATIONS

Anderson, Victor C "Sound Scattering from a Fluid Sphere", the Journal of the Acoustical Society of America, vol. 22, No. 4, p. 426, 1950.

(Continued)

*Primary Examiner* — Lisa Caputo
*Assistant Examiner* — Rose M Miller
(74) *Attorney, Agent, or Firm* — Perry+Currier Inc.

(57) ABSTRACT

Provided herein is a method to detect, characterize and classify a particle. A light source and an ultrasound transducer are controlled to irradiate the particle with light and an ultrasound pulse. A feature associated with the particle is determined by processing ultrasound data resulting from the particle being irradiated. The feature is compared to a reference to determine at least one property of the particle. According to some non-limiting implementations, the feature comprises a power spectrum of the particle. According to some non-limiting implementations, the ultrasound data is processed to determine characteristics in a range of about 100 MHz to about 1000 MHz of the power spectrum. According to some non-limiting implementations, the ultrasound pulse is in a range of about 100 MHz to about 1000 MHz. A computing device to detect, characterize and classify a particle is also provided.

24 Claims, 17 Drawing Sheets

(51) Int. Cl.
*G01N 29/46* (2006.01)
*G01N 21/17* (2006.01)

(52) U.S. Cl.
CPC ............... *G01N 2021/1706* (2013.01); *G01N 2021/1708* (2013.01); *G01N 2291/015* (2013.01); *G01N 2291/023* (2013.01); *G01N 2291/028* (2013.01)

(58) Field of Classification Search
CPC ....... G01N 2291/023; G01N 2291/028; G01N 21/1702; G01N 21/1706; G01N 21/1708
USPC ...... 73/601, 643, 61.71, 61.75, 61.79, 64.53
See application file for complete search history.

(56) References Cited

U.S. PATENT DOCUMENTS

| | | | |
|---|---|---|---|
| 2005/0085725 A1* | 4/2005 | Nagar | A61B 5/0095 600/437 |
| 2005/0187471 A1* | 8/2005 | Kanayama | A61B 5/0091 600/437 |
| 2007/0197886 A1* | 8/2007 | Naganuma | A61B 5/0095 600/322 |
| 2007/0220979 A1* | 9/2007 | Su | B82Y 15/00 73/643 |
| 2009/0156932 A1 | 6/2009 | Zharov | |
| 2009/0187099 A1* | 7/2009 | Burcher | A61B 5/0059 600/430 |
| 2011/0088477 A1* | 4/2011 | Someda | A61B 5/0095 73/641 |

OTHER PUBLICATIONS

Diebold, G. J., M. I. Khan, and S. M. Park. "Photoacoustic "signatures" of particulate matter: optical production of acoustic monopole radiation." Science 250.4977 (1990): 101-104.

Faran Jr., James J. "Sound Scattering by Solid Cylinders and Spheres". The Journal of the Acoustical Society of America, vol. 23, No. 4, pp. 405-418, 1951.

Maev et al "Principles of Local Sound Velocity and Attenuation Measurements Using Transmission Acoustic Microscope". IEEE Transactions on Ultrasonics, Ferroelectrics and Frequency Control, vol. 44, No. 6, pp. 1224-1231, Nov. 1997.

Strohm, Eric et al., Photoacoustic spectral characterization of perfluorocarbon droplets. Protons Plus Ultrasound: Imaging and Sensing 2012. Proc. of SPIE vol. 8223, 8223F, Feb. 9, 2012.

Roy, Ronald Aurele, Quantitative Particle Characterization by Scattered Ultrasound. Yale University, Faculty of the Graduate School, 1987.

Nedosekin, Dmitri A. et al., Ultra-fast photoacoustic flow cytometry with a 0.5 MHz pulse repetition rate nanosecond laser. Optics Express, vol. 18, No. 8, Apr. 12, 2010.

International Search Report, dared Apr. 29, 2013, PCT/CA2013/000212.

Strohm, Eric, "Determining the mechanical properties of apoptotic cells using time resolved acoustic microscopy" (2009). Theses and dissertations. Paper 944.

Strohm, Eric et al.: "Optical Droplet Vaporization of Micron-sized Perfluorocarbon Droplets and their Photoacoustic Detection", (2011). Proc. of SPIE vol. 7899, 78993H.

* cited by examiner

METHOD, SYSTEM AND APPARATUS FOR THE DETECTION, CHARACTERIZATION AND CLASSIFICATION OF PARTICLES USING PHOTOACOUSTIC AND ULTRASOUND TECHNIQUES

CROSS-REFERENCE TO RELATED APPLICATION

This application claims priority to U.S. application No. 61/696,455 filed on Sep. 4, 2012, the contents of which are incorporated herein by reference.

FIELD

The specification relates generally to the detection, characterization and classification of particles, and specifically to a method and system for the detection, characterization and classification of particles using photoacoustic and ultrasound techniques.

BACKGROUND

The identification, characterization and classification of different particles is an important task in many fields and industries, including medicine, materials science, pharmacology and electronics. Unfortunately, many of the currently known techniques can have undesirable side-effects and are limited to the identification, characterization and classification of only certain types of particles.

SUMMARY

The present specification provides a method to identify, characterize and classify particles using photoacoustic (PA) and/or ultrasound (US) analysis methods and accompanying systems. In some cases, the particles are 1-50 μm in diameter, which give unique PA and US spectral features in the about 100 MHz to about 1000 MHz frequency range. Particles can be biological-related such as cells, or microbubbles, liquids such as emulsions, or solids such as polymers, microbeads and plastics. When irradiated (i.e. interrogated) with a light beam, such as a laser or any other form of electromagnetic radiation, the particle emits an ultrasound wave (also referred to as a photoacoustic wave) that has characteristic spectral features that are unique to the shape, size and composition of the particle. In addition, when irradiated with an ultrasound pulse, the resulting scattered ultrasound waves from the particle have characteristic spectral features that are also unique to the shape, size and composition of the particle. The spectrum produced by the described PA/US methods and systems can be compared to a reference power spectrum, such as a control measurement or a established theory (for example, Diebold theory for photoacoustics, or Anderson or Faran theory for ultrasound) for particle identification.

Particle identification can be also performed using US and/or PA time domain signals (such as the amplitude or intensity). The presence or absence of a PA and an US signal can be used to determine if a particle is present in a sample. External additives such as dyes, nanoparticles or micrometer-sized beads can be added to a sample of particles, where these additives bind to specific particles. The ultrasound detects if a particle is present in the target area; the presence of a both a PA and US signal denotes that the additive was bound to the particle, and the absence of a PA signal, but presence of a US signal denotes no additive was bound to the particle. In this way, specific particle populations within a sample can be counted. Endogenous optical absorbers (such as melanin in melanocyte cells, hemoglobin in RBCs, or even DNA) can be used instead of external additives for label-free particle counting.

Flow cytometry is a significant application for this technology, where particles are streamed through a target area to be identified at high speed at rates of thousands of particles per second or more. Current flow cytometers use optical imaging, electrical impedance and light scattering methods to count and determine the size and volume of single particles. Optical fluorescence flow cytometry is often considered the gold standard for biological identification where cells are stained with a fluorescence dye. However these dyes can introduce cytotoxic effects and are generally used with fixed cells only. Moreover, fluorescence-based flow cytometers must be combined with another method to determine size, adding to their expense and complexity.

The described PA/US methods and systems may be used to rapidly count specific particles in a sample, and/or determine the size, morphology and properties of particles of many types, and examine individual live cells without staining, which could be advantageous over fluorescence-based flow cytometry methods and is a highly desired feature of flow cytometers. However, staining methods could be employed to increase sensitivity in cases where label-free methods cannot be used.

According to a first non-limiting implementation, there is provided a method to detect, characterize and classify a particle comprising: controlling a light source and an ultrasound transducer to irradiate the particle with light and an ultrasound pulse; determining a feature associated with the particle by processing ultrasound data resulting from the particle being irradiated; and comparing the feature to a reference to determine at least one property of the particle.

According to an aspect of the first non-limiting implementation, the feature comprises a power spectrum of the particle. According to a related non-limiting implementation, the reference comprises one or more of a control power spectrum and a theoretical model power spectrum. According to another related non-limiting implementation, the theoretical model power spectrum is based on one or more of an ultrasound scattering model, photoacoustic generation model or a finite element model.

According to another aspect of the first non-limiting implementation, the feature comprises one or more of an amplitude and an intensity of a pressure wave received by the ultrasound transducer.

According to another aspect of the first non-limiting implementation, the method further comprises using a light-based analysis technique to assist in determining the feature of the particle. According to a related non-limiting implementation, the light-based analysis technique comprises one or more of photoacoustics, fluorescence, light scattering, spatially localized light scattering, light transmission and absorbance.

According to another aspect of the first non-limiting implementation, the ultrasound transducer is configured to measure one or more of a photoacoustic wave and a pressure wave resulting from irradiation of the particle by the light and the ultrasound pulse. According to a related non-limiting implementation, the ultrasound data comprises data received from the ultrasound transducer when the ultrasound transducer is measuring the one or more of a photoacoustic wave and a pressure wave.

According to another aspect of the first non-limiting implementation, the ultrasound data comprises data resulting from detecting one or more of a photoacoustic pulse and an ultrasound pulse.

According to an aspect of the first non-limiting implementation, the ultrasound data is processed to determine characteristics in a range of about 100 MHz to about 1000 MHz of the power spectrum.

According to an aspect of the first non-limiting implementation, the ultrasound pulse is in a range of about 100 MHz to about 1000 MHz. According to another aspect of the first non-limiting implementation, the determining the feature comprises applying a Fast Fourier Transform (FTT) to the ultrasound data.

According to another aspect of the first non-limiting implementation, the ultrasound data is received from at least one transducer which in turn measures a received ultrasound pulse from the particle and converts the received ultrasound pulse to the ultrasound data and, further, the at least one transducer may comprise one or more of the ultrasound transducer and a further ultrasound transducer.

According to another aspect of the first non-limiting implementation, the ultrasound data is indicative of one or more of an ultrasound wave and a scattered ultrasound wave produced when the particle is irradiated.

According to another aspect of the first non-limiting implementation, controlling one or more of the light source and the ultrasound transducer to irradiate the particle comprises alternately irradiating the particle with one of the light and the ultrasound pulse and then the other of the light and the ultrasound pulse.

According to another aspect of the first non-limiting implementation, the particle comprises one or more of a solid particle, a solid spherical particle, a liquid particle, a liquid spherical particle and a gas particle.

According to another aspect of the first non-limiting implementation, the at least one property comprises one or more of a size, an orientation, a morphology and a composition of the particle.

According to another aspect of the first non-limiting implementation, the at least one property comprises one or more of a type, a count and a state of the particle.

According to another aspect of the first non-limiting implementation, the light source comprises a laser.

According to a second non-limiting implementation, there is provided a computing device to detect, characterize and classify a particle, comprising: a processing unit and a memory device, the processing unit enabled to: receive the input data and control a light source and an ultrasound transducer to irradiate the particle with light and an ultrasound pulse based on the input data, determine a feature associated with the particle by processing ultrasound data resulting from the particle being irradiated, and compare the feature to a reference stored at the memory device to determine at least one property of the particle.

According to an aspect of the second non-limiting implementation, the feature comprises a power spectrum of the particle.

According to an aspect of the second non-limiting implementation, the feature comprises one or more of an amplitude and an intensity of a pressure wave received by the ultrasound transducer.

According to an aspect of the second non-limiting implementation, the ultrasound transducer is configured to measure one or more of a photoacoustic wave and a pressure wave resulting from irradiation of the particle by the light and the ultrasound pulse. According to a related aspect of the second non-limiting implementation, the ultrasound data comprises data received from the ultrasound transducer when the ultrasound transducer is measuring the one or more of a photoacoustic wave and a pressure wave.

According to an aspect of the second non-limiting implementation, the ultrasound pulse is in a range of about 100 MHz to about 1000 MHz.

According to another aspect of the second non-limiting implementation, the determination of the feature comprises applying a Fast Fourier Transform (FTT) to the ultrasound data.

According to another aspect of the second non-limiting implementation, the ultrasound data is received from at least one transducer which in turn measures a received ultrasound pulse from the particle and converts the received ultrasound pulse to the ultrasound data and, further, the at least one transducer may comprise one or more of the ultrasound transducer and a further ultrasound transducer.

According to another aspect of the second non-limiting implementation, control of the light source and the ultrasound transducer to irradiate the particle comprises alternately irradiating the particle with one of the light and the ultrasound pulse and then the other of the light and the ultrasound pulse.

According to another aspect of the second non-limiting implementation, the light source comprises a laser.

BRIEF DESCRIPTIONS OF THE DRAWINGS

For a better understanding of the various implementations described herein and to show more clearly how they may be carried into effect, reference will now be made, by way of example only, to the accompanying drawings in which:

FIG. 3 further depicts one aspect of the orientation of a laser and ultrasound transducer(s) relative to an irradiated particle used in flow cytometry.

Figure 10:
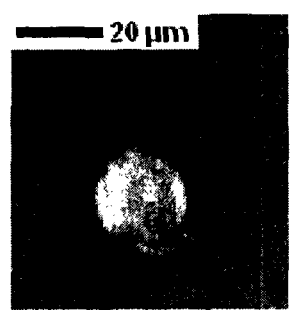
Figure 10:
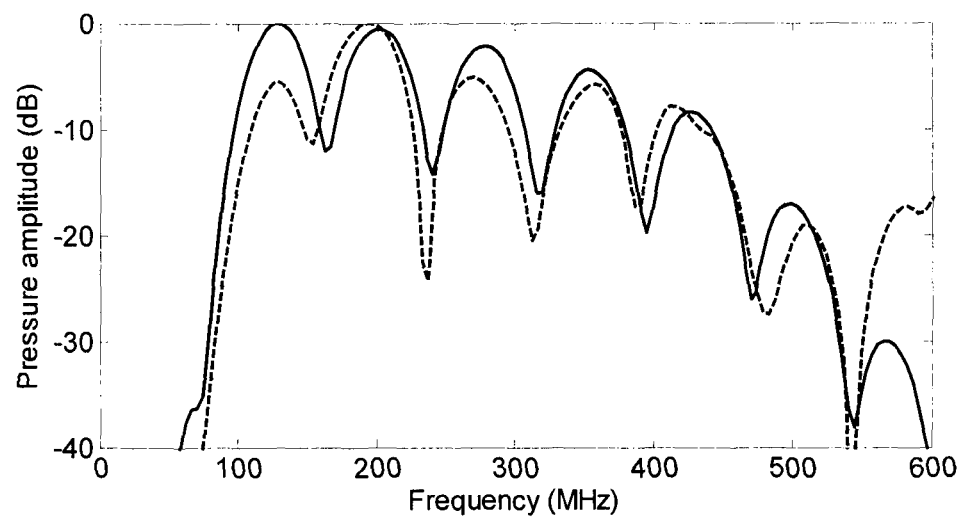
Figure 10:
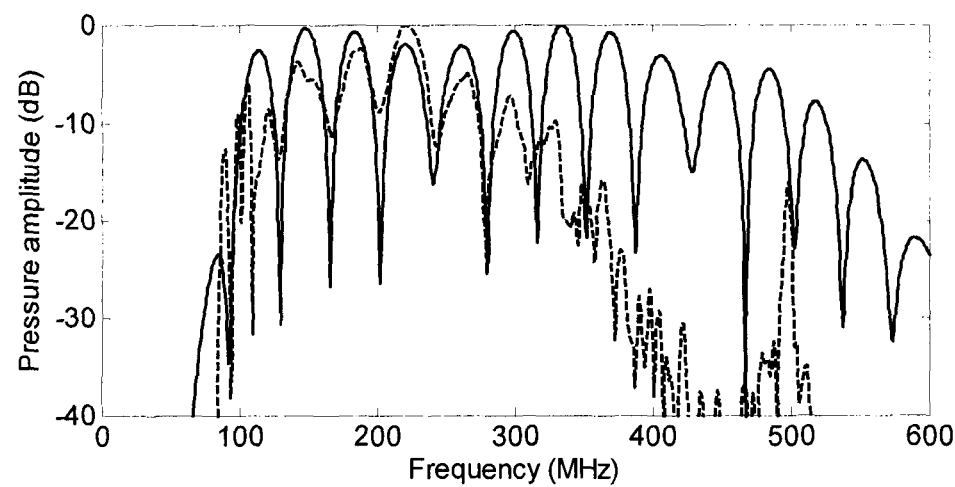

FIG. 10 depicts an optical measurement (photograph), photoacoustic (top graph) and ultrasound power spectra (bottom graph) of a melanoma cell compared to theory, according to a non-limiting implementation. In this implementation, the cell diameter was 21.7 µm (determined optically, see photograph) and the nucleus diameter was 18.0 µm (determined from fluorescence). Melanoma cells typically have optical absorbing melanin particles throughout the cytoplasm, but not the nucleus. By fitting the measured data (dotted line) to theory (solid line), the sound speed was 1560 m/s and the density was 1050 kg/m$^3$.

Figure 11:
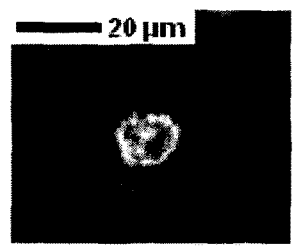
Figure 11:
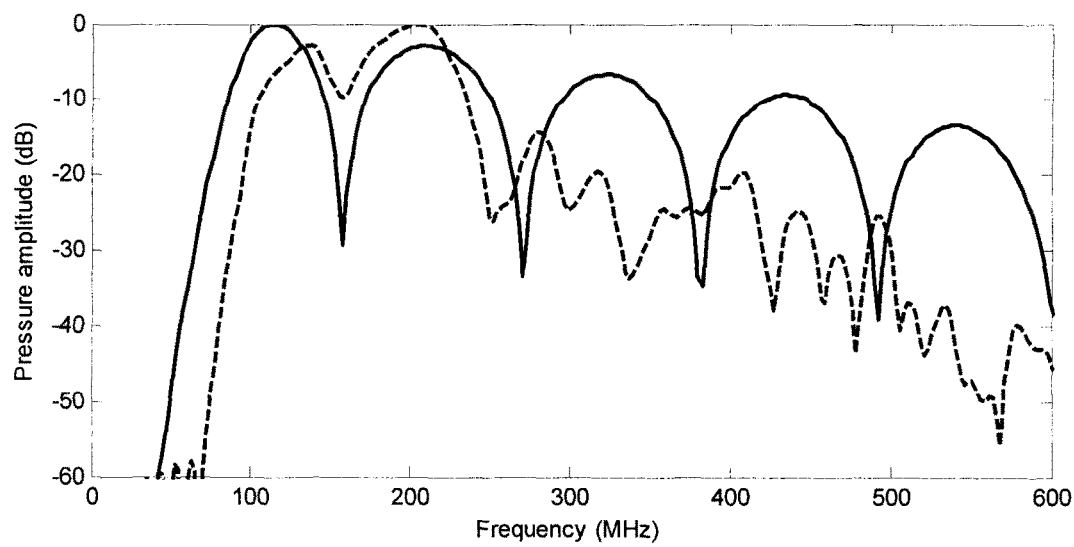
Figure 11:
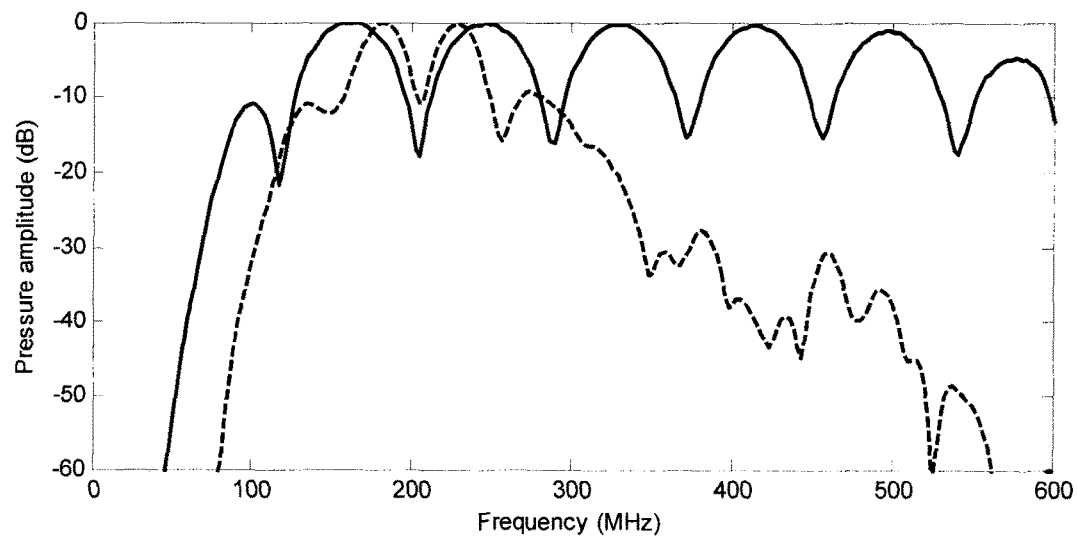

FIG. 11 depicts optical (photograph), photoacoustic (top graph), and ultrasound (bottom graph) measurements of a malignant (MCF7) cell compared to theory, according to non-limiting implementations, where the cell was stained with trypan blue. In this implementation, the cell diameter was 13.7 µm (determined optically). By fitting the measured data to theory, the sound speed was 1565 m/s and the density was 1045 kg/m$^3$.

Figure 12:
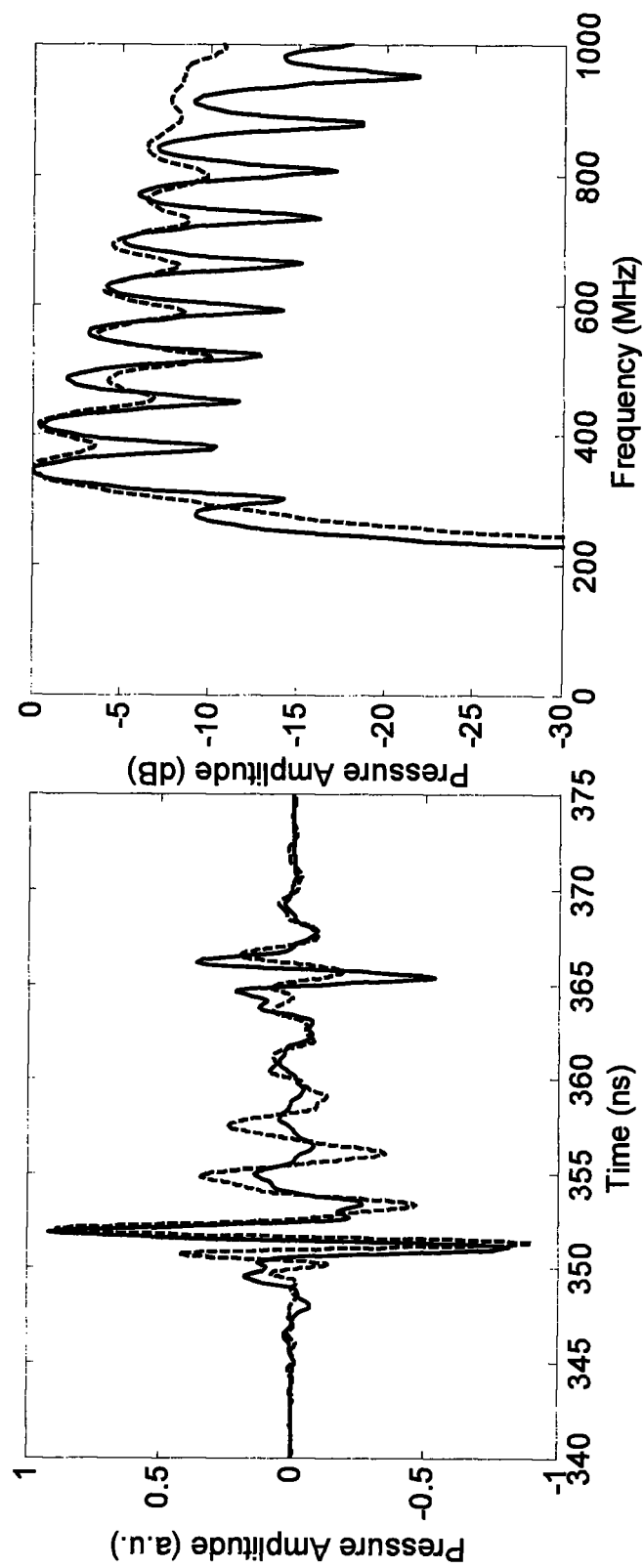

FIG. 12 depicts the measured (dotted line) and theoretical (solid line) photoacoustic pressure waveform (left graph) and spectrum (right graph) of a 2.45 µm perfluorocarbon emulsion measured with a 750 MHz ultrasound transducer, according to a non-limiting implementation. In this implementation, excellent agreement between measured values and theory were observed, supporting the methodology. The size was confirmed optically.

Figure 13:
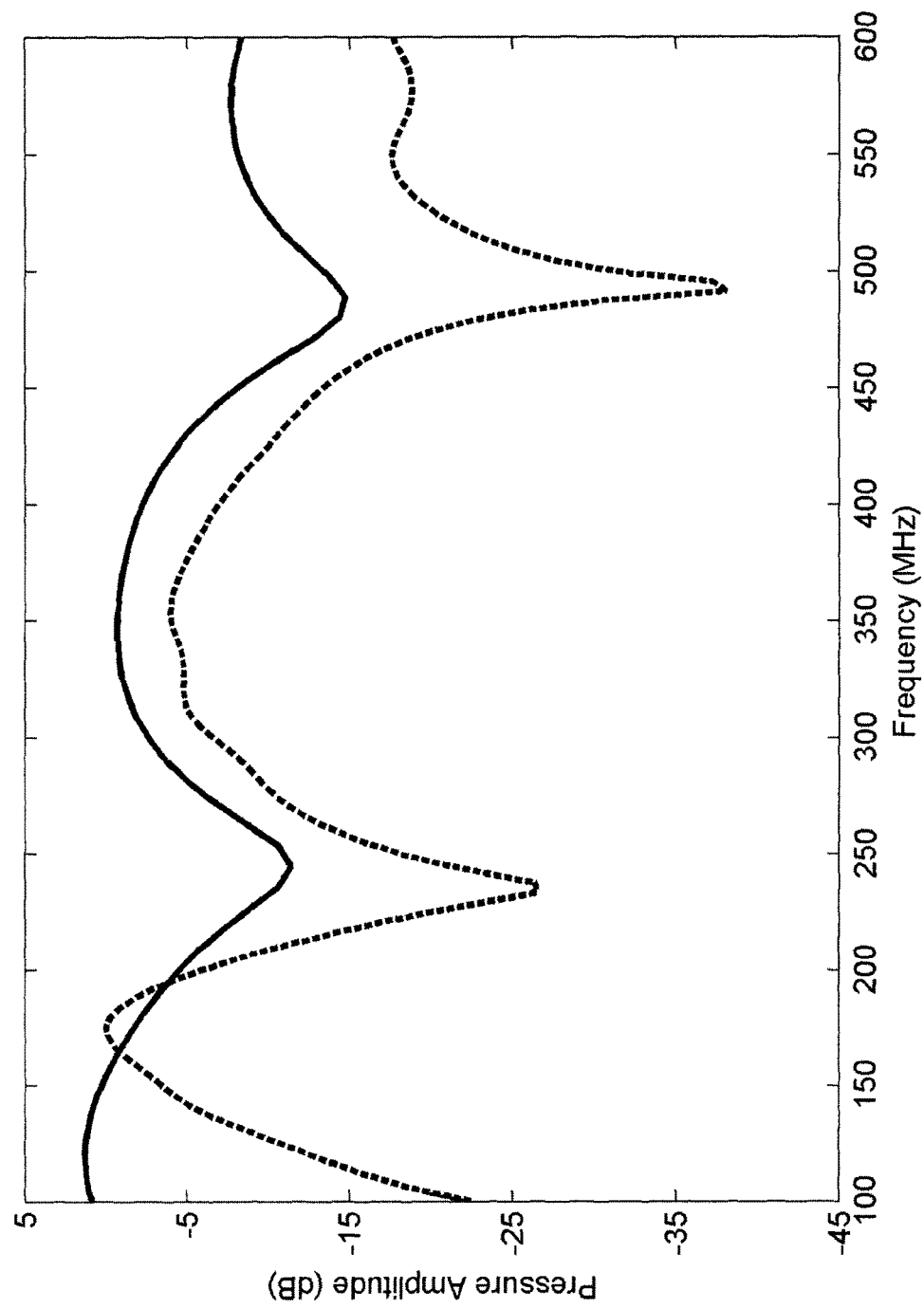

FIG. 13 depicts the measured (dotted line) and theoretical (solid line) photoacoustic power spectrum of a RBC measured according to a non-limiting implementation. The RBC was oriented so that the long edge was towards the ultrasound transducer.

Figure 14:
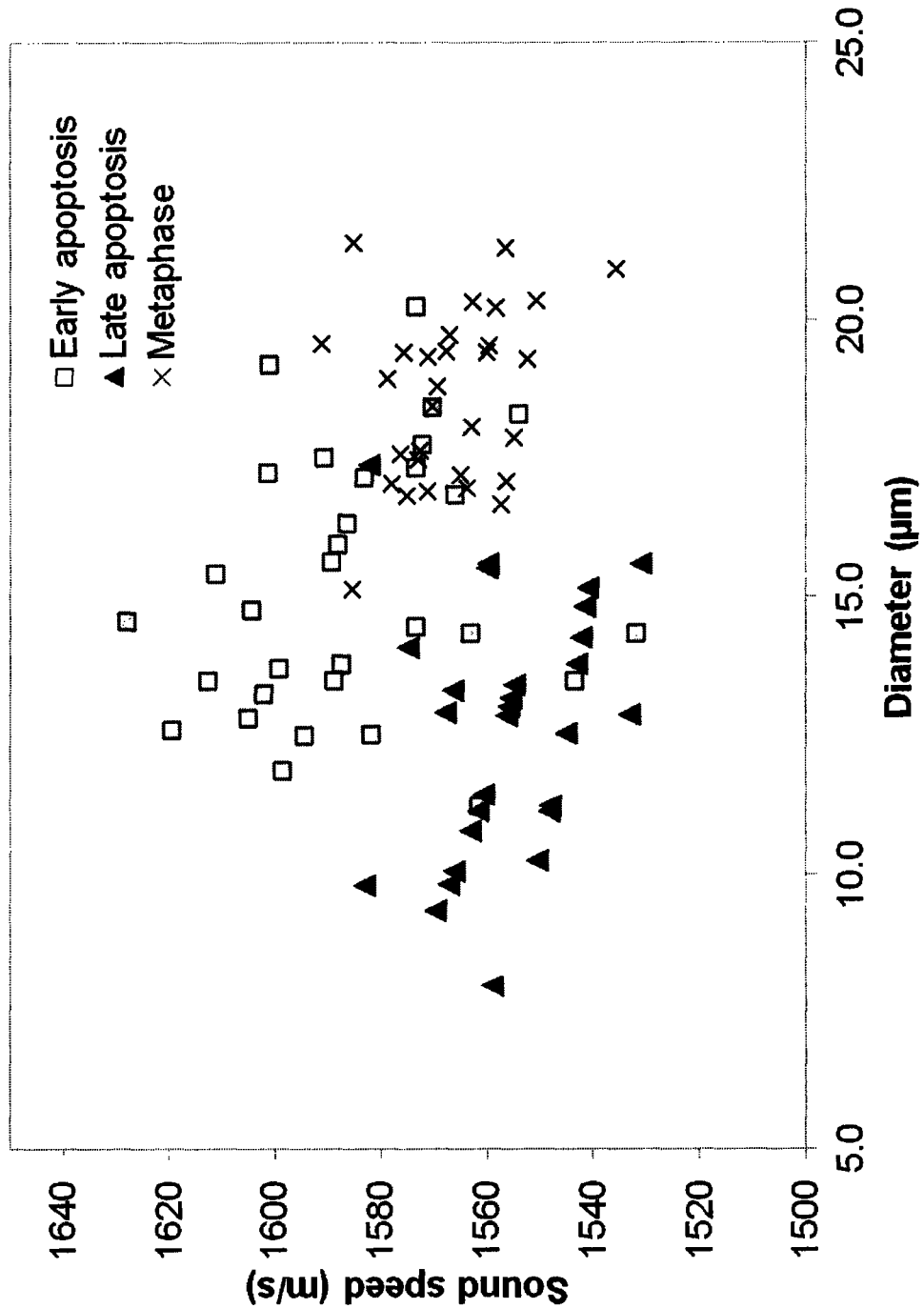

FIG. 14 depicts how particle identification, according to non-limiting implementations, could be used to differentiate between cells in different states, such as early, late stage apoptosis and mitosis using parameters obtained from the described PA/US spectral methods and systems.

Figure 15:
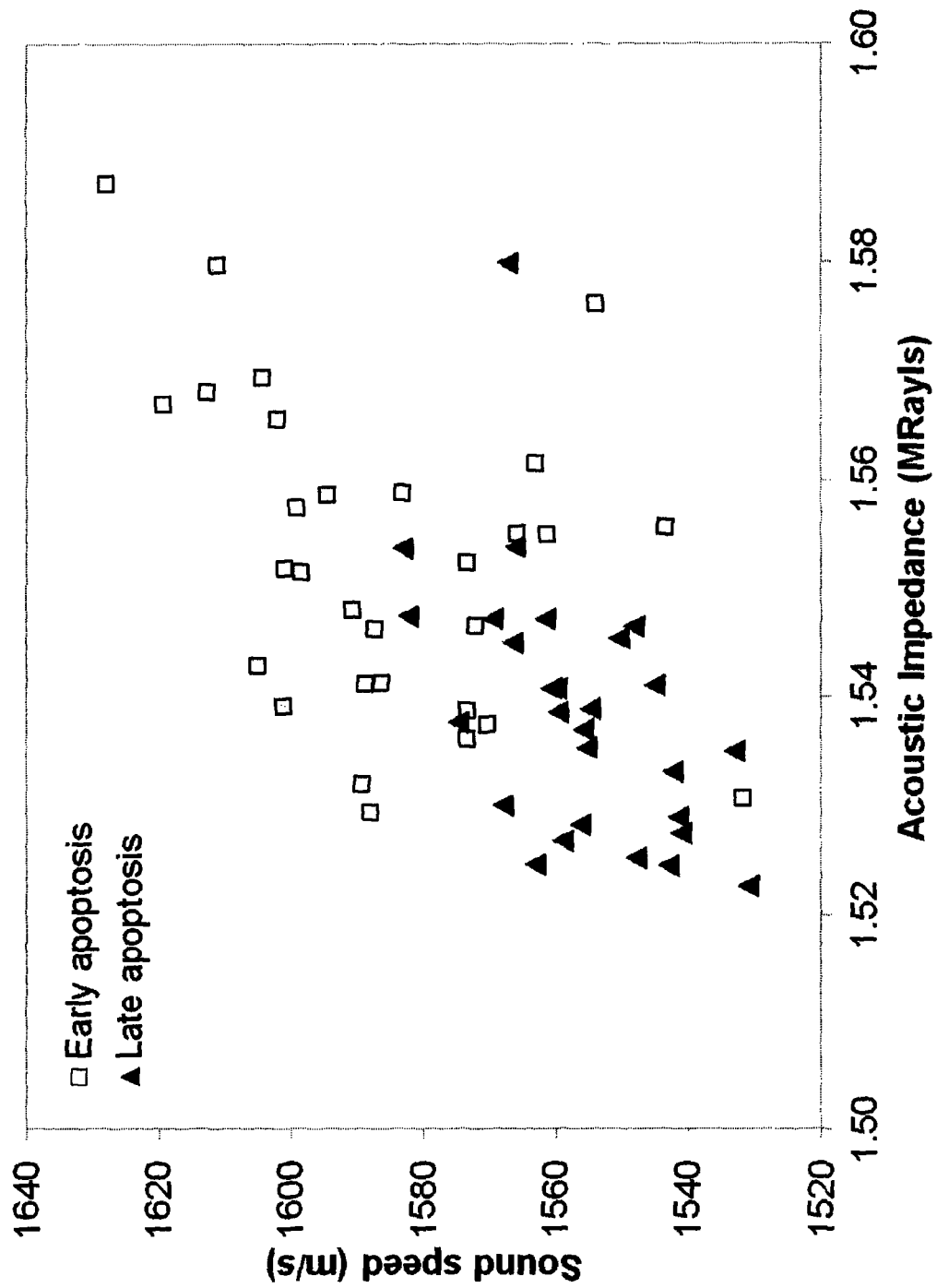

FIG. 15 depicts how particle identification, utilizing non-limiting implementations, could be used to differentiate between cells in different states, such early and late stage apoptosis using parameters obtained from PA/US spectral methods and the transmission ultrasound measurements.

Figure 16:
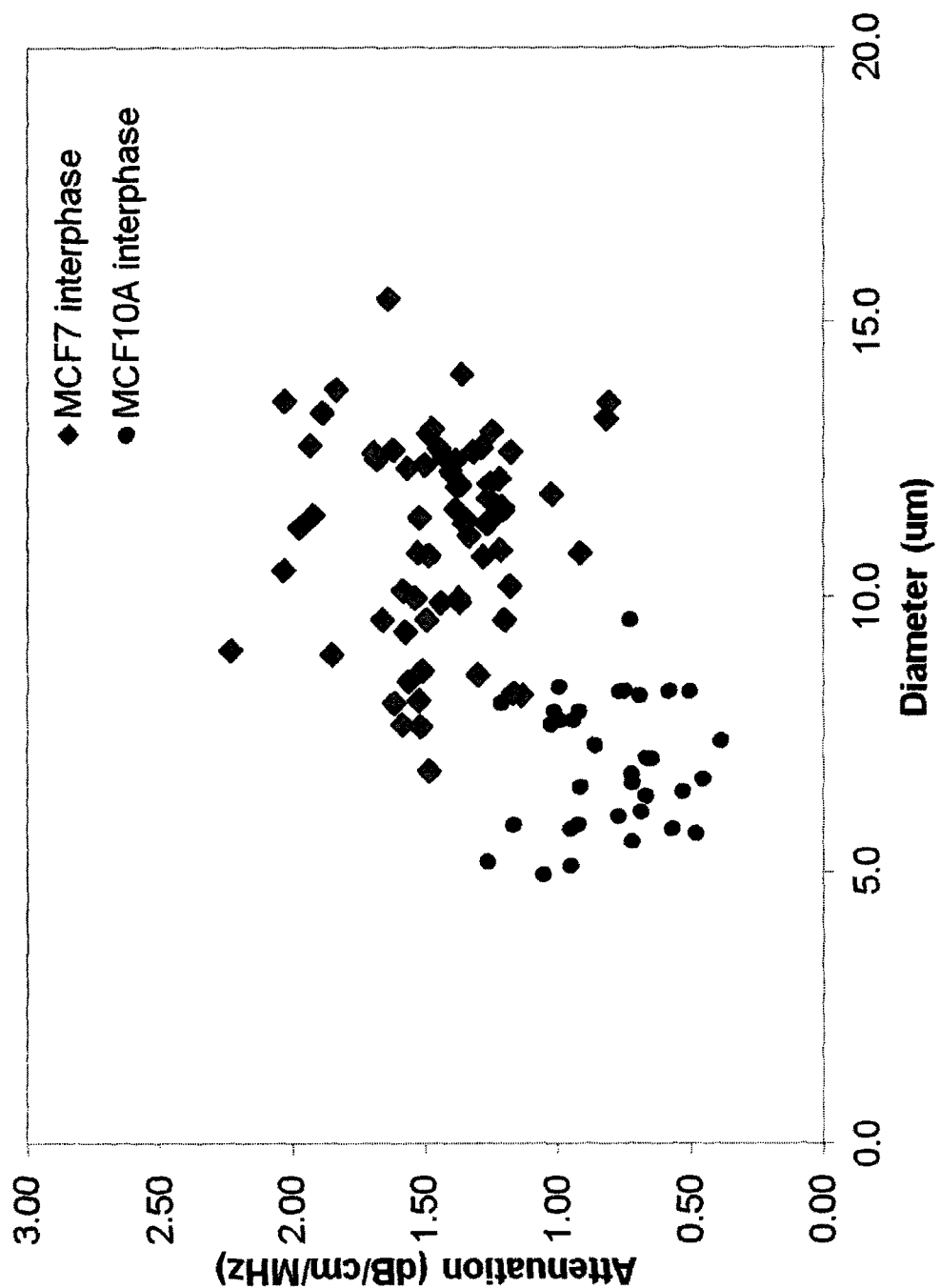

FIG. 16 depicts how particle identification, utilizing non-limiting implementations, could be used to differentiate between different types of cells, such as malignant (MCF7) and benign (MCF10A) breast cells using parameters obtained from PA/US spectral methods and the transmission ultrasound measurements.

Figure 17:
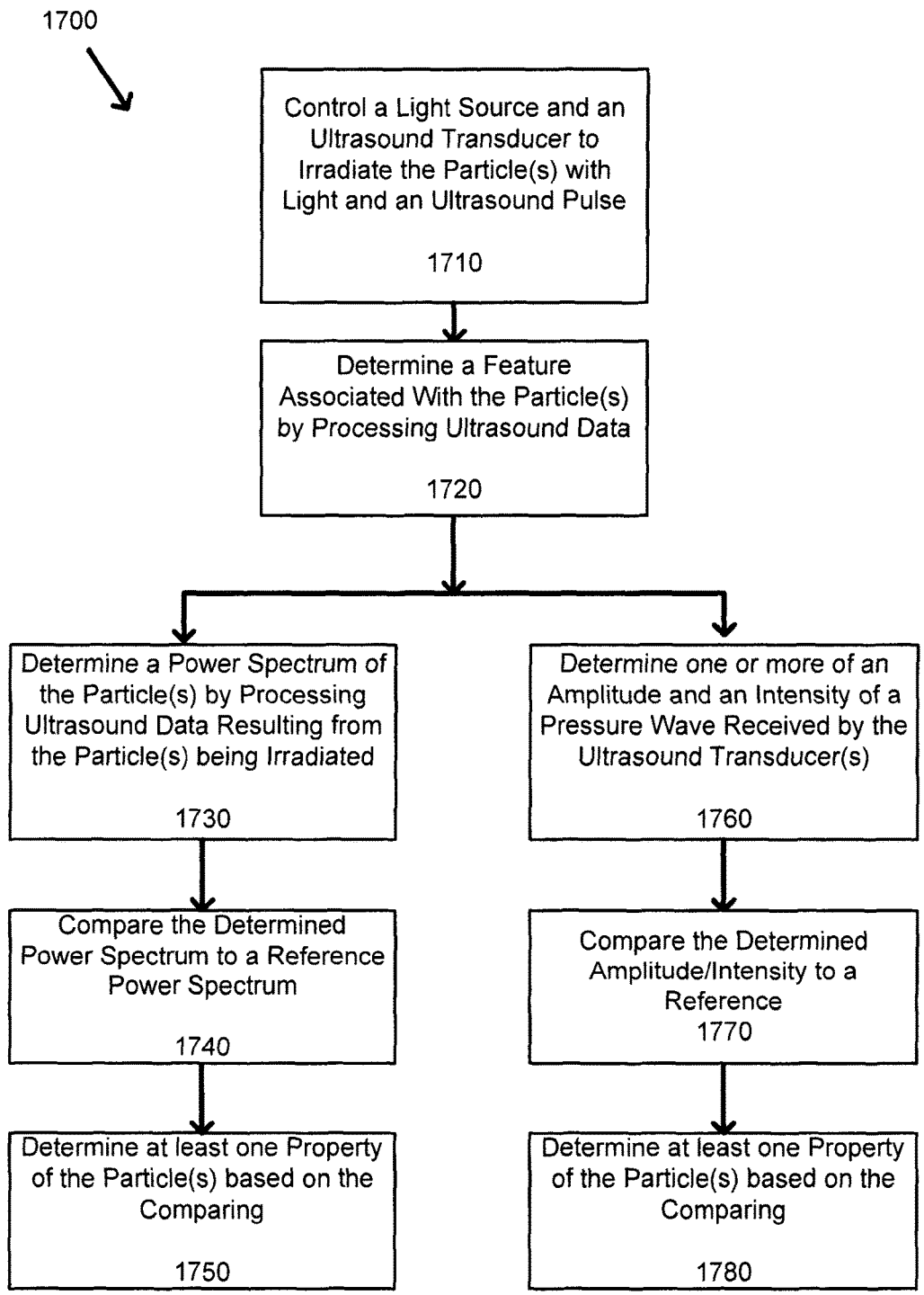

FIG. 17 depicts a flowchart of a method for detecting and classifying particles, according to non-limiting implementations.

DETAILED DESCRIPTION

Figure 1:
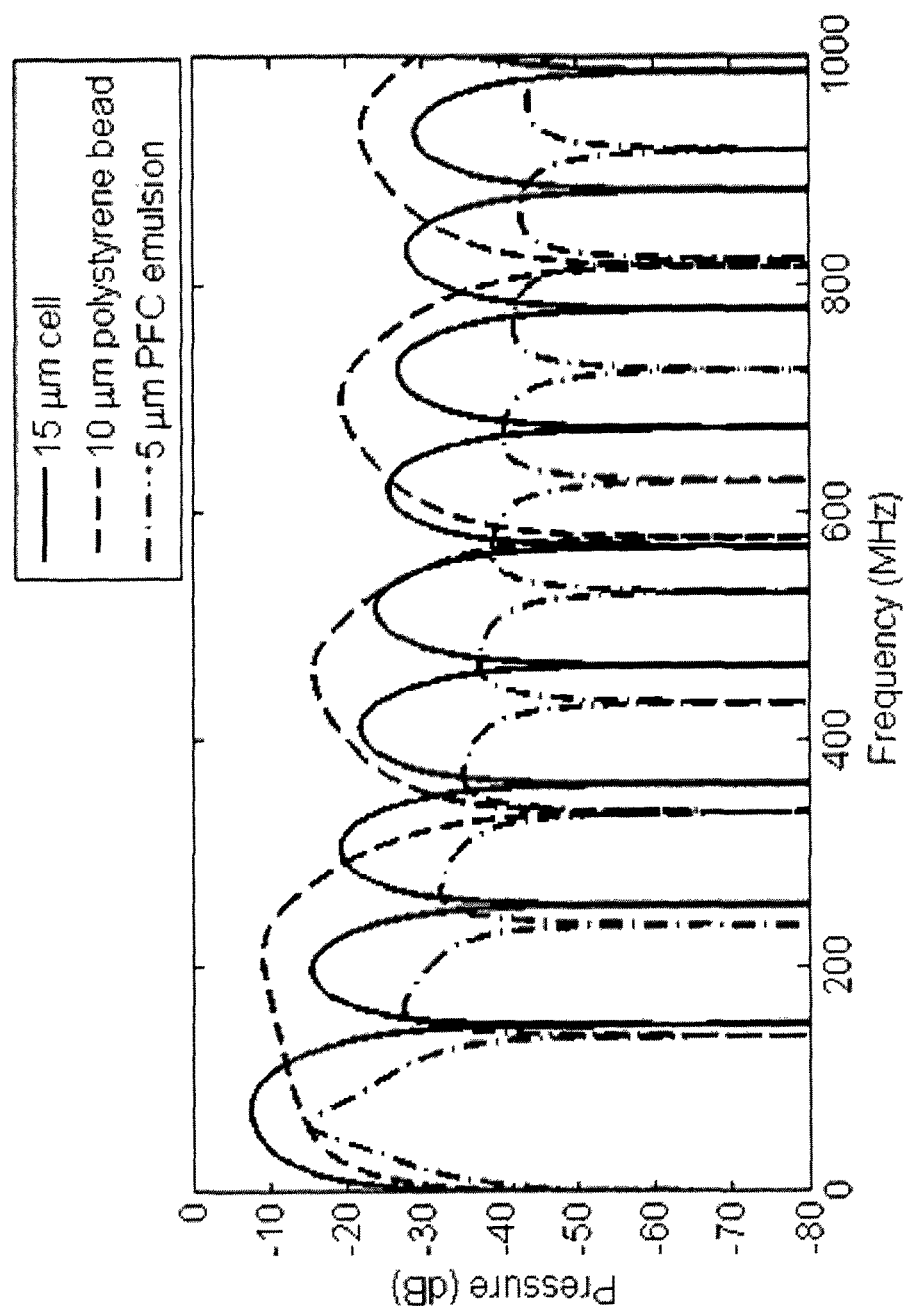
FIG. 1 depicts the theoretical photoacoustic power spectrum from particles with different compositions, including biological cells, polystyrene microbeads and perfluorochemical (PFC) emulsions.
Figure 2:
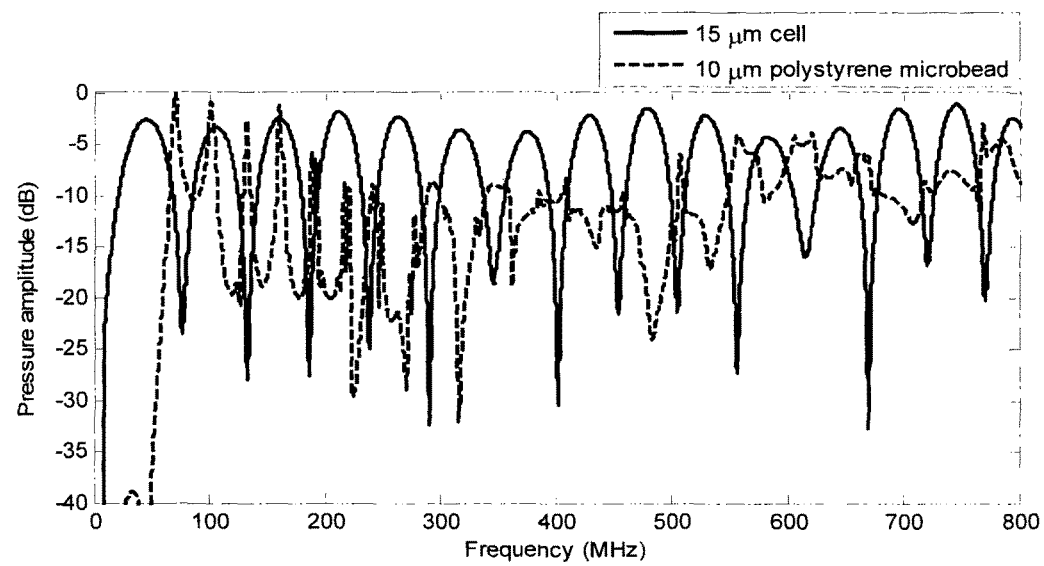
FIG. 2 depicts the theoretical ultrasonic backscatter power spectrum (top graph) and ultrasonic sidescatter power spectrum (bottom graph) from particles with different compositions, such as a biological cell and a polystyrene microbead, according to non-limiting implementations.
Figure 2:
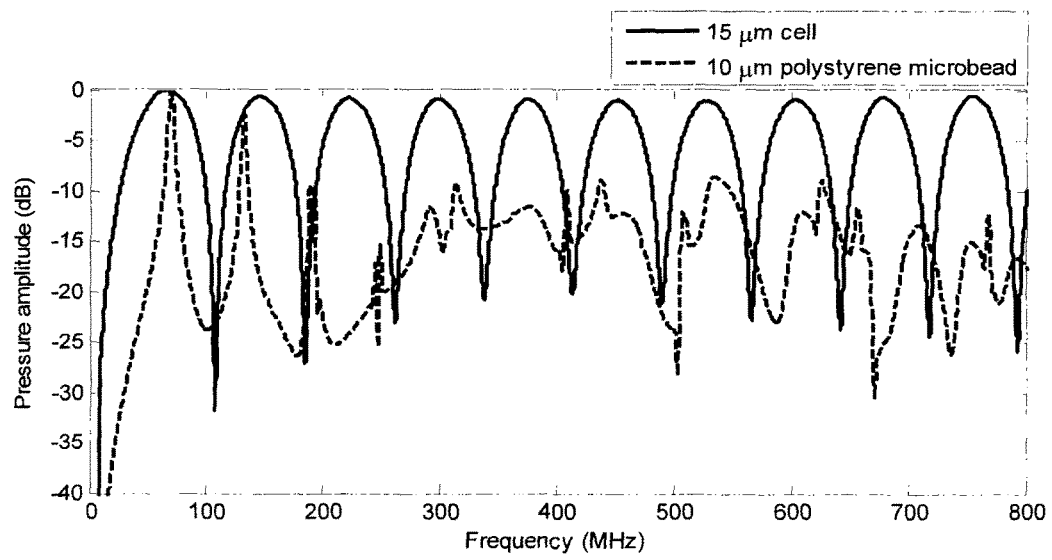

The PA/US analysis methods and systems described herein can be used to identify particles in a sample. The time domain pressure wave (e.g. the US and/or PA amplitude or intensity) can be used to detect the presence or absence of a particle. When irradiated by a US pulse, the particle will reflect some US away from the particle. The presence of this scattered signal signifies that a particle is present. The particle can then be irradiated by a laser. If the particle absorbs the laser energy, a PA pressure wave will be emitted. The presence or absence of this PA wave can be used to classify the particle (e.g. determine the type of particle). PA/US spectral methods can also be used to identify particles in the 1-50 µm diameter range, where both the photoacoustic and ultrasonic power spectra have unique features or characteristics such as periodic minima and maxima that vary as much as 20 dB when using frequencies in the range of up to about 1000 MHZ, including, but not limited to, a range of about 100 MHz to about 1000 MHz (see see FIGS. 1 and 2). Particles in this size range generally have featureless photoacoustic power spectra below 100 MHz (where most measurements are typically performed), and therefore the power spectra cannot be used to uniquely identify particles. However, particles of nearly any type can be examined with the described PA/US methods and systems. Non-limiting examples of particles that can be characterized by methods described herein include biological samples (eukaryotic cells, red blood cells, stem cells, etc.), emulsions, gas particles (such as microbubbles), polymers and plastics, and/or any particles that are about 1 µm to about 50 µm in diameter. The theory behind the photoacoustic and ultrasonic spectral methods and systems is presented below.

For clarity, reference herein to a "PA/US" spectral method can refer to utilizing of one or more of photoacoustic and ultrasonic techniques since multiple methods can be used for particle identification. For example, particles can be irradiated with light, such as laser light, to generate ultrasound waves, such as photoacoustic pressure waves, and/or the particles can be irradiated with an ultrasound pulse to generate scattered ultrasound waves. In other non-limiting examples, both a light source and ultrasound transducer could be used to generate ultrasound waves and scattered ultrasound waves, where the particle is irradiated simultaneously and/or sequentially (e.g. alternately) with light and an ultrasound pulse. The power spectra from any or all of these methods can be used for particle identification.

In other non-limiting examples, the PA and/or US signals could be combined with other light based analysis techniques to assist in determining a feature of the particle. For example, light based analysis techniques could involve light-sensitive sensors to detect fluorescence, light scattering, spatially localized light scattering (e.g. optical coherence tomography (OCT) and derivatives), light transmission and/or absorbance. According to some example implementations, the PA/US analysis methods and systems described herein have been applied to particles within the 1-50 µm size range and 100-1000 MHz frequency range, however any size could be examined over any frequency range. In particular, larger particles may have unique spectra at lower frequencies, or particles with unique compositions may have spectral features outside of the expected 100-1000 MHz range.

It is noted that while the term "light" is used in this description to refer to human visible wavelengths of light (e.g. about 390 nm to about 750 nm), any source of electromagnetic radiation, including but not limited to light, microwaves, radio waves, heat and the like, could be used to induce the particle or particles to emit the described ultrasound wave or ultrasound waves.

Figure 3:
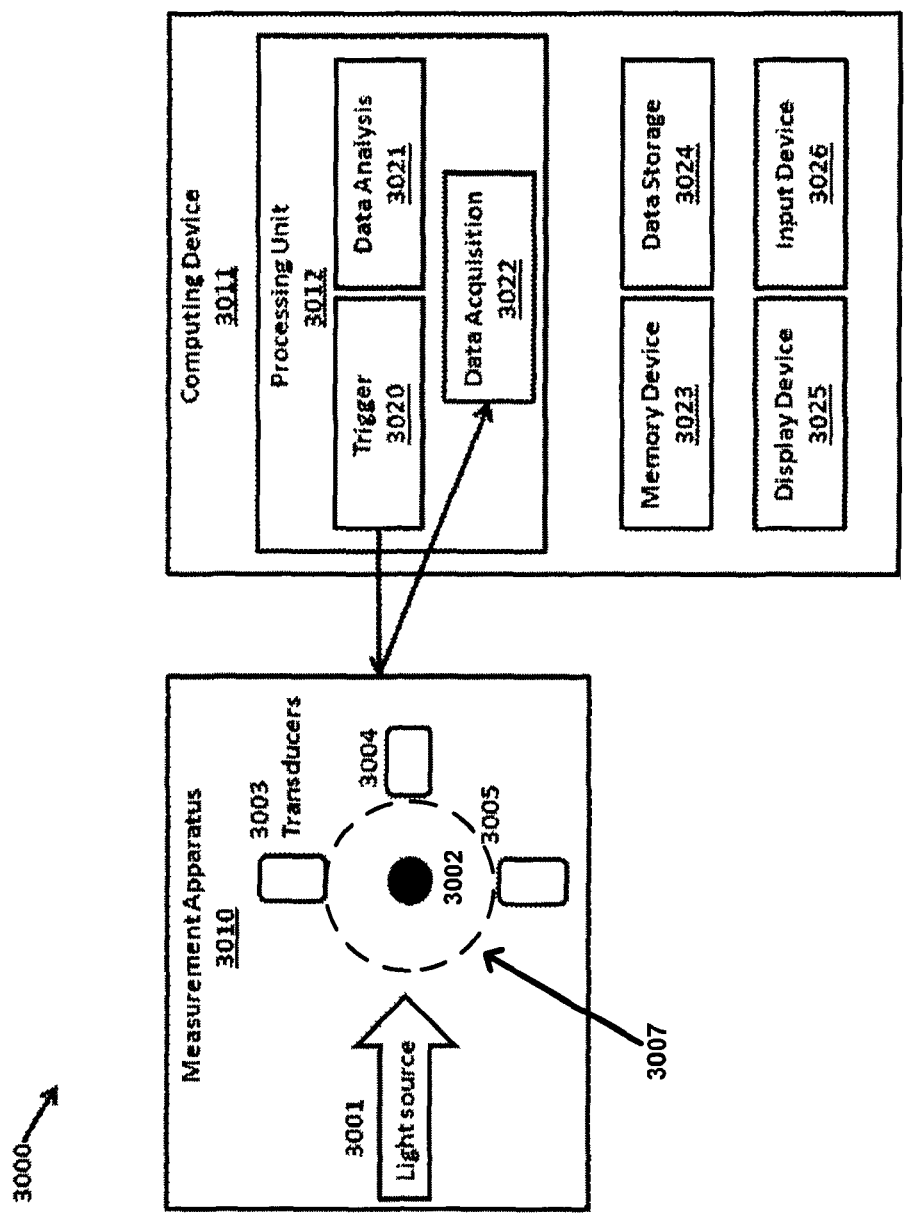
FIG. 3 depicts a system to detect and classify a particle, according to non-limiting implementations.

Attention is directed to FIG. 3, which depicts a system 3000 for detecting and classifying a particle according to non-limiting embodiments. Measurement apparatus 3010 retains particle 3002 to be measured; measurement apparatus 3010 comprises detectors for detecting photoacoustic and/or ultrasonic waves (in this case, ultrasound transducers 3003, 3004 and 3005). A light source 3001, which can comprise, for example, a laser or any broadband or narrowband source, irradiates (e.g. illuminates) particle 3002 generally located within target area 3007.

Although target area 3007 is depicted in FIG. 3 as a circular region of a particular size, it is understood that target area 3007 can comprise any geometry and size suitable for irradiating particle 3002 using light source 3001 and/or one or more of ultrasound transducers 3003-3005.

Upon irradiation, particle 3002 absorbs the light energy which results in the emission of one or more broadband ultrasound waves (e.g. pressure wave(s) with frequencies ranging from kHz to GHz), that radiate outwards from particle 3002. One or more of ultrasound transducers 3003-3005 detect and record the ultrasound wave(s) emitted from particle 3002 as a result of the irradiation by light source 3001. Then an ultrasound pulse is emitted from at least one of ultrasound transducers 3003-3005, and the ultrasound wave scattered from particle 3002 as a result of the irradiation by at least one of transducers 3003-3005, is detected by all of the surrounding ultrasound transducers 3003-3005.

Computing device 3011, in communication with measurement apparatus 3010, is enabled to control, record and trigger light source 3001 and ultrasound transducers 3003-3005. Computing device 3011 comprises processing unit 3012, which is enabled to trigger (i.e. control) light source 3001 and ultrasound transducers 3003-3005, by way of trigger 3020. Trigger 3020 can hence comprise one or more of a command signal, control data or trigger data that that is transmitted by processing unit 3012 to light source 3001 and ultrasound transducers 3003-3005 to control light source 3001 and ultrasound transducers 3003-3005 to irradiate particle 3002.

Processing unit 3012 also comprises data acquisition system 3022, which acquires data, including ultrasound data resulting from particle 3002 being irradiated, and data analysis system 3021, which performs data analysis computations. In some implementations, trigger 3020 also triggers data acquisition by data acquisition system 3022. In some implementations, trigger 3020 causes data acquisition system 3022 to record data from light source 3001 and ultrasound transducers 3003-3005. In some implementations, trigger 3020 causes data acquisition system 3022 to record data after trigger 3020 causes light source 3001 and ultrasound transducers 3003-3005 to irradiate particle 3002. In some implementations, trigger 3020 causes data acquisition system 3022 to record data, and light source 3001 and ultrasound transducers 3003-3005 to irradiate particle 3002, simultaneously.

Data received from measurement apparatus 3010 is processed (e.g. digitized) by data acquisition system 3022, and can be stored in memory device 3023 and/or saved to data storage device 3024, for longer-term storage or backup reasons. In some implementations, computing device 3011 does not comprise data storage device 3024; rather data, including ultrasound data, is stored at memory device 3023. Alternatively, in some implementations, computing device 3011 does not comprise memory device 3023; rather data, including ultrasound data, is stored at data storage device 3024. In some implementations, computing device 3011 comprises a desktop computer. In some implementations, computing device 3011 comprises dedicated hardware designed exclusively for measurement apparatus 3010. In some implementations, computing device 3011 comprises a portable electronic device, including, but not limited to, a laptop computer. In some implementations, computing device 3011 may be enabled to communicate with measurement apparatus wirelessly.

For clarity, particle 3002 is depicted in FIG. 3 as a single particle, however, in some implementations a plurality of particles can be examined, for example, by providing a stream of particles passing through target area 3007. As such, it is understood that references made to particle 3002 can also refer to a plurality of particles 3002.

Furthermore, although three ultrasound transducers are depicted in FIG. 3, more or less than three ultrasound transducers can be utilized. As a non-limiting example, a single ultrasound transducer can be used to both irradiate particle 3002 and detect/record the emitted ultrasound wave(s). As another non-limiting example, more than three ultrasound transducers can be utilized to irradiate and detect/record the ultrasound wave(s), for example at different angles. When more than one ultrasound transducer is used, in one implementation, one ultrasound transducer can be used to irradiate particle 3002 and the remaining ultrasound transducer(s) can be used to detect/record the emitted ultrasound wave(s). Alternatively, in some implementations, all of the ultrasound transducers can be used to both irradiate particle 3002 and detect the emitted ultrasound wave(s). It is further appreciated that other variations and combinations of the ultrasound transducer(s) functionality and are within the scope of present implementations. Furthermore, in order to perform a light-based analysis technique to assist with determining a feature of the particle and thus a property of the particle, such as the particle type and state (e.g. whether the particle is a live or a dead cell), optical sensors or detectors could be used in place of an ultrasound transducer, including but not limited to optical sensors or detector capable of sensing/detecting fluorescence, light scattering, spatially localized light scattering (e.g. optical coherence tomography (OCT) and derivatives), absorbance/transmittance, and performing other related detecting/sensing.

Respectively, memory 3023 and data storage 3024 can comprise any suitable memory device, including but not limited to any suitable one of, or combination of, volatile memory, non-volatile memory, random access memory (RAM), read-only memory (ROM), hard drive, optical drive, flash memory, magnetic computer storage devices (e.g. hard disks, floppy disks, and magnetic tape), optical discs, and the like. Other suitable memory devices are within the scope of present implementations.

Data that results from the measurement (i.e. post-processing analysis system 3021) can be output to display 3025. A user can control computing device 3011 via input device 3026. Input device 3026 is generally enabled to receive input data, and can comprise any suitable combination of input devices, including but not limited to a keyboard, a keypad, a pointing device, a mouse, a track wheel, a trackball, a touchpad, a touch screen and the like. Other suitable input devices are within the scope of present implementations. Within target region 3007, particles 3002 can be stationary or flowing (for example, through a tube) where particle 3002 can be measured sequentially as in flow cytometry.

In non-limiting implementations using photoacoustics to detect and classify particle 3002, particle 3002 is situated near the focal regions of light source 3001, such as a pulsed laser, and one or more of ultrasound transducers 3003-3005 (FIG. 3). When illuminated by light source 3001, particle 3002 emits an ultrasound wave with frequencies that may range from kHz to GHz, such as a photoacoustic pressure wave or ultrasound pressure wave, where one or more of ultrasound transducers 3003-3005 situated around particle 3002 detect the emitted pressure wave, such as an ultrasound wave. In to some implementations, one or more ultrasound transducers 3003 to 3005 are configured to measure one or more of a photoacoustic wave and a pressure wave (e.g. ultrasound wave) resulting from irradiation of particle 3002 by the light and the ultrasound pulse.

A feature associated with the particle, such as a power spectrum of the particle, can be determined from the emitted ultrasound wave (as received/detected by one or more of ultrasound transducers 3003-3005). The resulting photoacoustic power spectrum has spectral features that are unique to the particle size, shape and composition. The resulting photoacoustic power spectrum is compared to a reference power spectrum, which can be based upon either (or both) a control sample which has known properties, or theory. For example, for a spherical particle, the Diebold model can be used, where the photoacoustic pressure wave amplitude P as a function of frequency f when irradiated with a laser intensity $I_0$ is:

$$P(f) = iA \frac{(\sin q - q \cos q)/q^2}{\left(1 - \frac{\rho_d}{\rho_f}\right)(\sin q/q) - \cos q + i\frac{c_d}{c_f}\frac{\rho_d}{\rho_f}\sin q} \text{ where} \quad (1)$$

$$q = \frac{2\pi f a}{c_d}, \text{ and } A = \left(\frac{\mu_a I_0 c_d \beta}{4\pi C_p (r/a)}\right) \quad (2)$$

where $\alpha$ is the particle diameter, $\rho$ is the density, c is the sound speed, $\beta$ is the particle thermal expansion coefficient, $C_p$ is the particle heat capacity, $\mu_a$ is the optical absorption coefficient, and the subscripts d and f refer to the particle and surrounding fluid, respectively. For non-spherical particles such as red blood cells (RBC), the measured power spectra can be compared to theoretical predictions found using other methods, such as finite element models (FEM). The parameters in equation (1) can be fitted to the measured photoacoustic power spectrum, where the parameters in A affect the spectral amplitude (such as absorption coefficient, and thermal properties), and the other parameters (diameter, sound speed, density) affect the location of the spectral minima and maxima. For non spherical particles such as RBCs, a FEM can be used instead of the analytical solution presented.

Other features associated with particle 3002 can be determined based on the emitted pressure wave (e.g. photoacoustic wave or ultrasound wave). For example, the amplitude of the ultrasound wave indicated by the amplitude of the resulting ultrasound signal, is proportional to the absorption coefficient $\mu_a$ of the dye used. The presence or absence of an ultrasound signal amplitude can be used to identify if a dye is present in the particle. The intensity of the ultrasound wave, indicated by the signal intensity, can be used to determine the amount of dye present in the particle. The ultrasound signal amplitude in either the time domain or frequency domain signal can be used for particle detection as they are related through transform operations.

In non-limiting implementations of using ultrasonics to detect and classify particle 3002, particle 3002 is situated near the focal regions of one or more of ultrasound transducers 3003-3005. Particle 3002 is irradiated by one or more ultrasound pulses emitted by one or more ultrasound transducers 3003-3005. These ultrasound pulses are scattered by particle 3002 (FIG. 3). The scattered ultrasound wave(s) are detected by one or more of ultrasound transducers 3003-3005 situated around particle 3002 (for example, backscatter, forward scatter, side scatter or any other angle). The ultrasound power spectrum can be compared to a reference power spectrum, based upon either (or both) a control measurement or theory. For example, for a spherical liquid particle, the Anderson model describes the scattered ultrasound wave as a function of angle, which depends on the particle size, and ratios of the sound speed and density between the particle and coupling fluid, respectively. In another example, for a solid spherical particle, the Faran model describes the theoretical scattered ultrasound wave as a function of angle and depends on the particle size, Poisson ratio and ratios of the sound speed and density between the particle and coupling fluid, respectively. In cases where the transverse sound speed is equal to zero (such as in liquids), the Faran model reduces to the Anderson model. In both cases, the theoretical power spectrum is fitted to the measured power spectra using the variables of equation (1) as parameters (sound speed, density, size, Poisson ratio). The amplitude of the ultrasound wave, as indicated by the resulting ultrasound signal, amplitude can signify the presence or absence of a particle, or detect external agents attached to the particle (such as beads, nanoparticles, etc.). In these cases, either the time domain or frequency domain ultrasound pressure signal could be used for particle detection.

Figure 4:
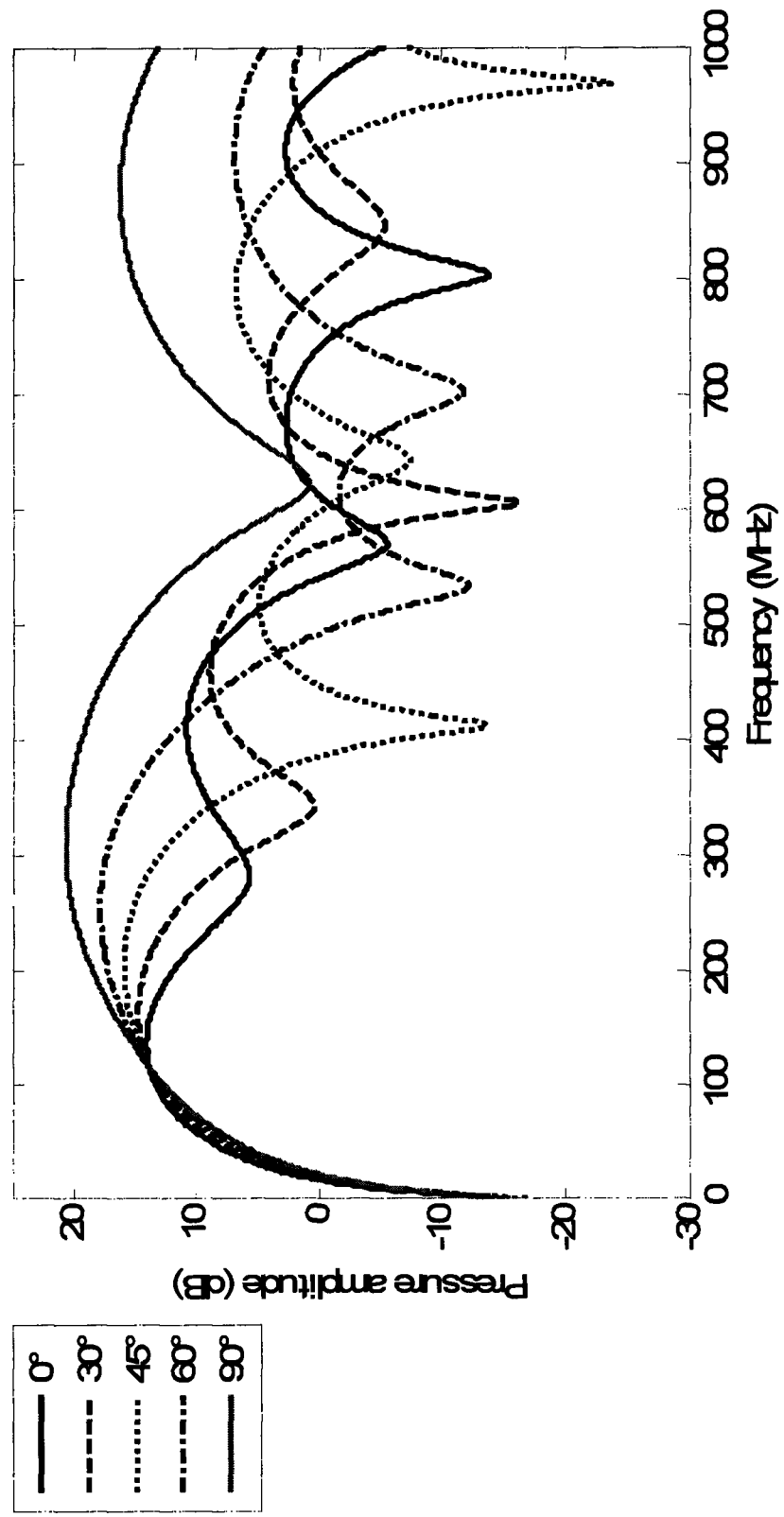
FIG. 4 depicts a photoacoustic power spectrum of a single 7 μm diameter red blood cell (RBC) based on theory (using finite element method calculations), according to non-limiting implementations. The RBC is oriented with the flat/narrow section of the RBC towards the transducer at 90°, and oriented with the long edge of the RBC towards the transducer at 0°.

In some implementations, a plurality transducers can be used as the resulting ultrasound waves from particle 3002 can be asymmetric and strongly dependent on the morphology and composition of particle 3002. For example, the photoacoustic power spectrum of an asymmetric bi-concave shaped RBC depends on its orientation relative to an ultrasound transducer (it is noted that a finite element model calculation was used to produce the photoacoustic power spectrum shown in FIG. 4), and the ultrasound wave scattered from a spherical cell depends on the position of transducers 3003-3005 relative to the position of at least one irradiating transducer (being one or more of ultrasound transducers 3003 to 3005) (for example, as in FIG. 2).

Figure 5:
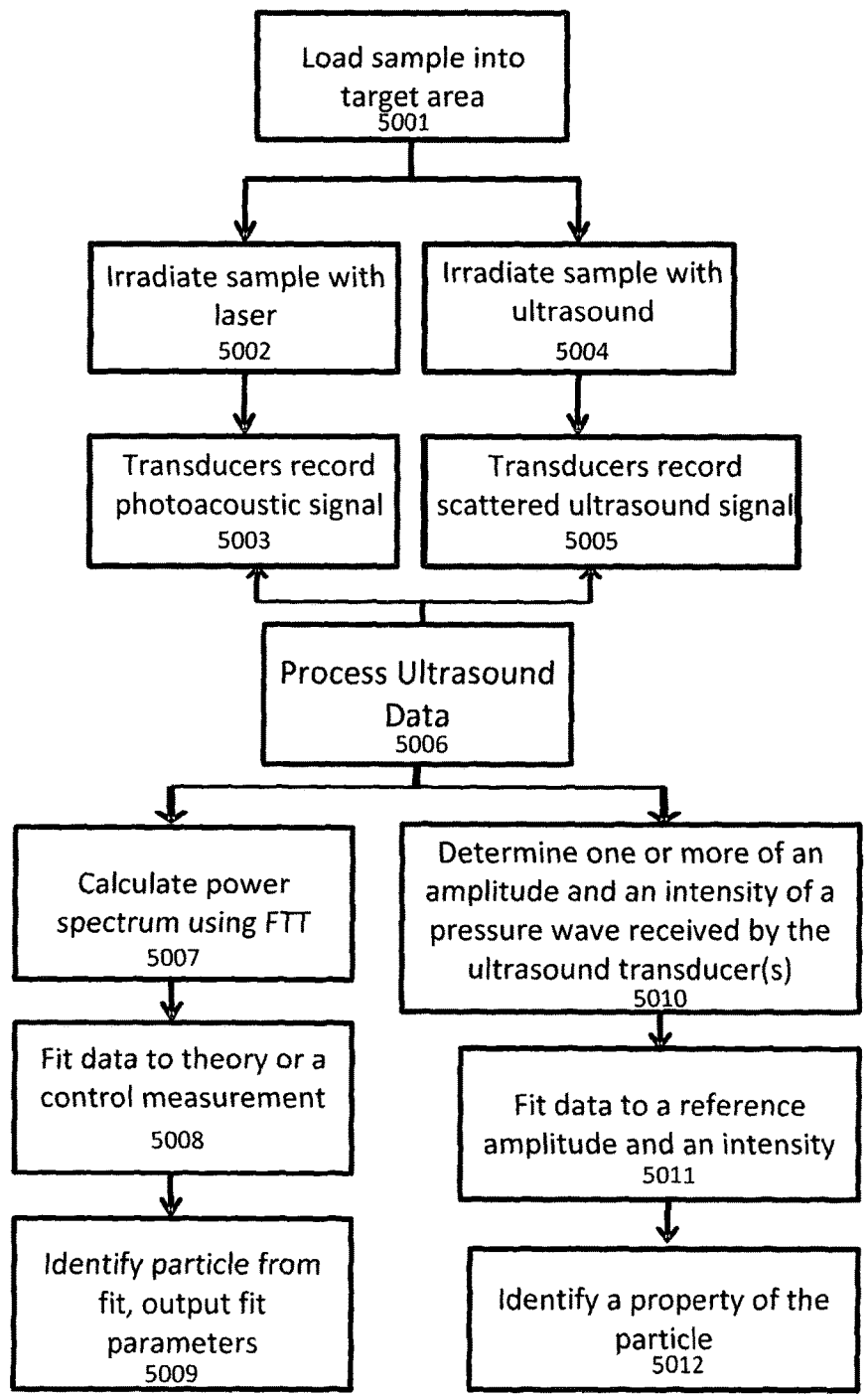
FIG. 5 depicts a flowchart of a method for detecting and classifying particles, according to non-limiting implementations.

Attention is next directed to FIG. 5 which depicts a flowchart of a method 5000 for detecting and classifying a particle according to a non-limiting implementation. In order to assist with the explanation of method 5000, it will be assumed that method 5000 is performed using system 3000. Furthermore, the following discussion of method 5000 will lead to a further understanding of system 3000 and it various components. However, it is to be understood that system 3000 and/or method 5000 can be varied, and need not work exactly as discussed herein in conjunction with each other, and that such variations are within the scope of present implementations.

It is to be emphasized, however, that method 5000 need not be performed in the exact sequence as shown, unless otherwise indicated; and likewise various blocks may be performed in parallel rather than in sequence; hence the elements of method 5000 are referred to herein as "blocks" rather than "steps". It is also to be understood, however, that method 5000 can be implemented on variations of system 3000 as well.

At block 5001, particle 3002 is loaded (e.g. positioned) within target area 3007, where light source 3001 and ultrasound transducers 3003-3005 are focused. As described hereafter, in non-specific implementations, light source 3001 comprises a laser. When both ultrasound and photoacoustic methods are used, particle 3002 can be alternately and/or sequentially irradiated by laser pulses from light source 3001 and ultrasound pulses from one or more of ultrasound transducers 3003-3005 at blocks 5002 and 5004. At blocks 5003 and 5005, one or more of ultrasound transducers 3003-3005 surrounding particle 3002 detect and record the resulting photoacoustic and ultrasound waves sequentially. As part of blocks 5003 and 5005, the one or more of ultrasound transducers convert the resulting photoacoustic waves or pressure waves into ultrasound data (e.g. photoacoustic and scattered ultrasound signals). In to some implementations, the ultrasound data comprises data received from one or more of ultrasound transducers 3003-3005 when the one or more of ultrasound transducers 3003-3005 is measuring the photoacoustic wave and/or pressure wave. In to some implementations, the ultrasound data is received from at least one of ultrasound transducers 3003-3005, which in turn measures a received ultrasound pulse from particle 3002 and converts the received ultrasound pulse into the ultrasound data. According to some implementations, the ultrasound data is indicative of one or more of an ultrasound wave and a scattered ultrasound wave produced when the particle is irradiated.

At block 5006, the ultrasound data is processed at processing unit 3011 to determine (e.g. calculate) a feature associated with particle 3002, such as an amplitude and an intensity of a pressure wave received by one or more of ultrasound transducers 3003-3005. Other features associated with particle 3002 can be determined by processing the ultrasound data, including a power spectrum of particle 3002. For example, at block 5007, a power spectrum of particle 3002 can be calculated using a Fast Fourier Transform (FTT). At blocks 5008 and 5009, properties of particle 3002, such as the size, morphology and composition of particle 3002, are determined by fitting the variables in the theoretical equations to the measured photoacoustic and ultrasound spectra. The composition is a function of particle size, sound speed, density and elasticity which are parameters in the theoretical equations, and are unique for each type of particle. Alternatively, properties of particle 3002 are determined by comparing the measured phtotoacoustic and ultrasound spectra with a control sample of known properties.

As another example, at block 5010, one or more of an amplitude and an intensity of the emitted pressure wave received by one or more of ultrasound transducers 3003-3005, indicated by the resulting ultrasound signal, can be determined based on the processing of the ultrasound data. At blocks 5011 and 5012, the determined amplitude and/or determined intensity can be compared to a reference, such as a reference data set or a control sample to identify a property of particle 3002. Identified properties can include particle type (e.g. whether particle 3002 is a red blood cell), a count of particle 3002 (to, for example, count the total number of particular red blood cells exist in a sample) and a state, such as whether particle 3002 is a live cell or a dead cell.

The processing of ultrasound data could occur in tandem with the particle measurements. Referring to FIG. 3, the measured ultrasound waves from particle 3002 could be recorded and converted to a power spectrum via Fast Fourier Transform (FFT) accessible by data analysis device 3021, then saved to memory device 3023 or a stored to data storage device 3024. The determined power spectrum could then be compared to a reference power spectrum based on theory or a control reference file, which could stored by memory device 3023 or by data storage device 3024, or even computed in real time by data analysis device 3021. From this comparison, the size and morphology, and properties such as the sound speed, density and elasticity of particle 3002 can be determined.

These parameters can be found using different methods. As a non-limiting example, the entire determined power spectrum could be compared to a database of power spectra using various algorithms such as correlation functions or a goodness of fit. As another example, key features of the determined power spectrum at various frequencies (e.g. 200, 300 and 400 MHz) could be found using the amplitude, slope, mid-band fit and y-intercept.

When using two ultrasound transducers that are situated opposite each other (such as ultrasound transducers 3003 and 3005 in FIG. 3), transmission ultrasound measurements can be used to determine properties of particle 3002 such as the sound speed, acoustic impedance, density, bulk modulus and attenuation. The size of particle 3002 can be found through other methods, such as from the PA/US spectral method, or from the change in the ultrasound data (e.g. acoustic signal) as particle 3002 passes through an ultrasound pulse produced by one or more of ultrasound transducers 3003-3005 or a laser beam produced by light source 3001 (an example signal extinction method is described below). For the acoustic impedance and attenuation, spectral methods can be used to determine the change in these parameters as a function of frequency. The parameters found using the transmission ultrasound measurements can complement the parameters found using the PA/US spectral method by reaffirming the values obtained (such as the sound speed and density), or by adding new information (such as the acoustic impedance, bulk modulus and attenuation).

Detailed Example Implementations

Provided below are descriptions of example implementations of the described PA/US spectral methods and systems as reduced to practice. These examples are provided for illustrative purposes and to facilitate understanding of the described PA/US spectral methods and systems. It is understand that these examples are not specifically limiting variations thereof and are within the scope of the claimed implementations.

In a first example implementation, all measurements were performed using a SASAM™ photoacoustic microscope (from Kibero, GmbH of Saarbruecken, Germany). This device comprises an optical inverted microscope (Olympus IX-81) with an ultrasound transducer positioned above a sample stage. The microscope enables optical viewing of sample (e.g. a particle or particles) from below, and ultrasound and photoacoustic measurements using an ultrasound transducer positioned above the sample. A laser collimated into the microscope was focused onto the sample by the same optical objective used to view the sample. The laser can be focused to a 5-20 μm spot size, depending on the numerical aperture. The optical view also allows for precise targeting of the ultrasound transducer to the sample, and alignment of the laser and ultrasound transducer. One or more particles under flow are simulated by moving the sample stage through the target area while the ultrasound transducer and laser remain stationary.

Figure 6:
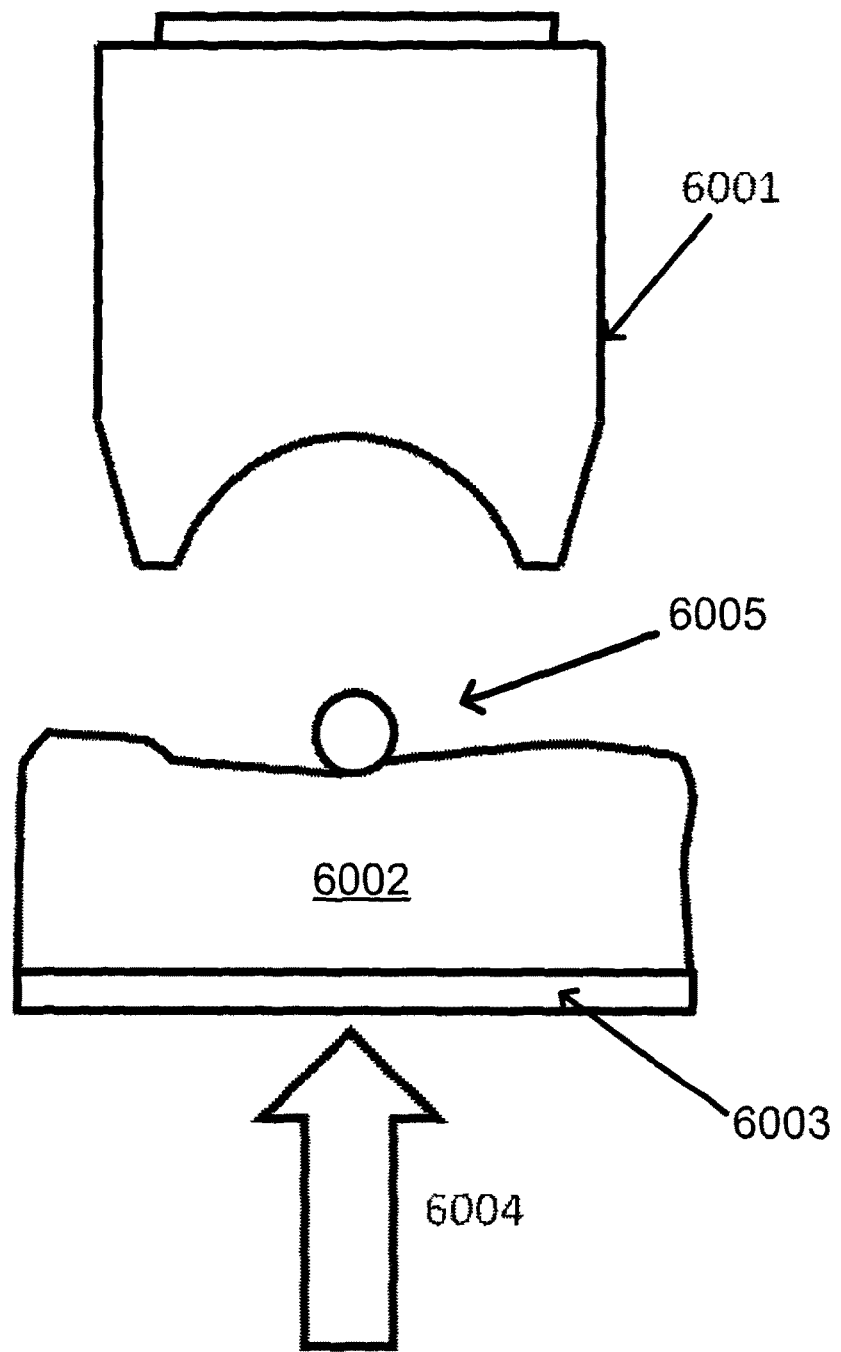
FIG. 6 depicts a schematic diagram showing how particles in suspension were measured according to a non-limiting implementation. In this implementation, the culture dish was coated with a thin layer of 1% agar to prevent back reflections from the substrate.
Figure 7:
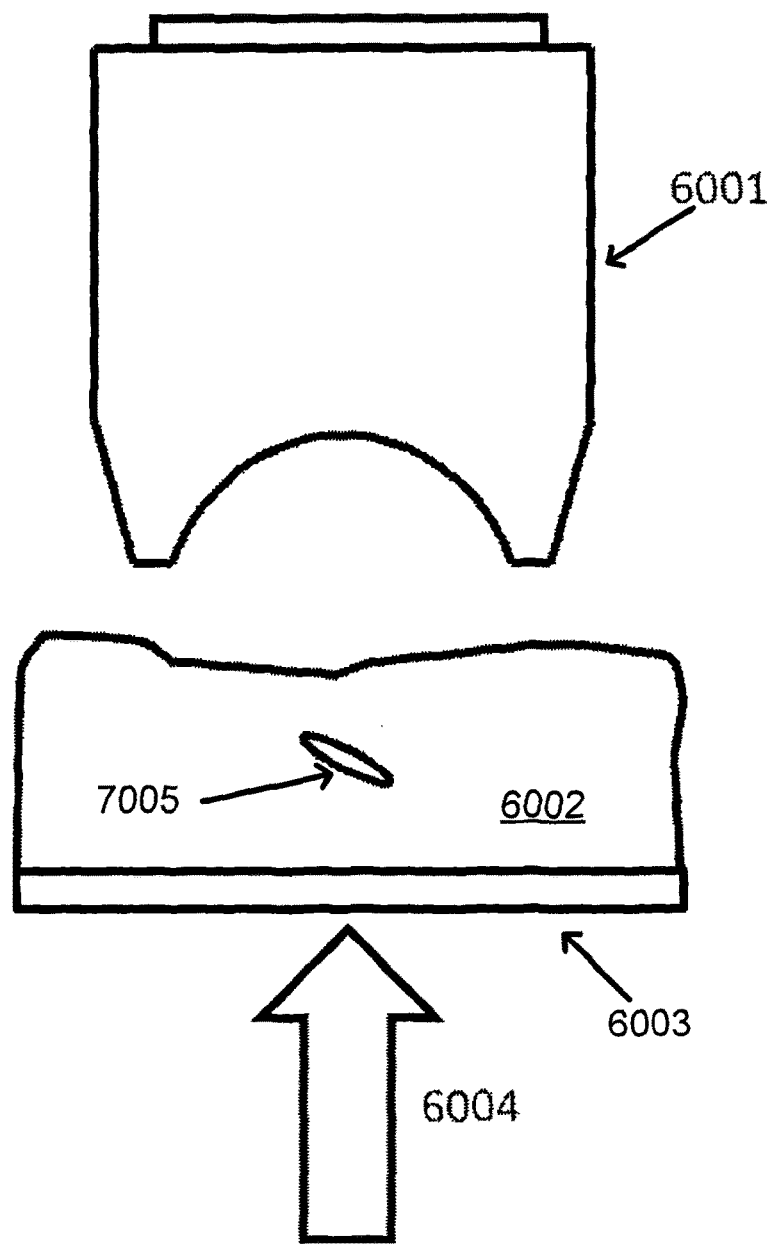
FIG. 7 depicts a diagram showing how irregular shaped particles (such as RBCs) were measured according to a non-limiting implementation. In this implementation, the particles were immobilized in a gelatin phantom to preserve their position and orientation relative to the transducer.

A schematic of a typical measurement of a sample particle according to this example implementation is shown in FIG. 6, where particle 6005 is located on top of thin agar phantom 6002 to reduce ultrasound echoes from substrate 6003. Transducer 6001 is focused onto particle 6005 from above, and laser 6004 is focused onto particle 6005 from below. In some implementations, the sample particle or particles are embedded inside thin agar phantom 6002 to restrict movement, such as when measuring the waves from asymmetric particles like RBCs (see, for example, particle 7005 in FIG. 7 having a similar setup as in FIG. 6 with like elements having like numbers). In the examples described herein, the particles (6005, 7005) were either on top of phantom 6002 or embedded within phantom 6002; then sample stage 6003 was moved at a specific speed to simulate particles (6005, 7005) under flow.

In a second example implementation, a SASAM™ photoacoustic microscope was equipped with two main ultrasound transducers; an ultrasound transducer with a 200 MHz center frequency (42% −6 dB bandwidth, f#=1) and with a 375 MHz ultrasound transducer center frequency (40% −6 dB bandwidth, f#=1). All measurements were amplified by 40 dB and digitized at 8 GHz. Ultrasound pulse repetition frequencies up to 500 kHz were used. In this example implementation, two lasers were used for these measurements, a 532 nm and 1064 nm laser with energies up to approximately 0.5 µJ/pulse when focused onto the sample. The two lasers had a pulse width of <1 ns and pulse repetition frequencies of up to 4 kHz. In further alternative implementations, tunable lasers can be used with pulse repetition frequencies higher than 4 kHz.

Figure 8:
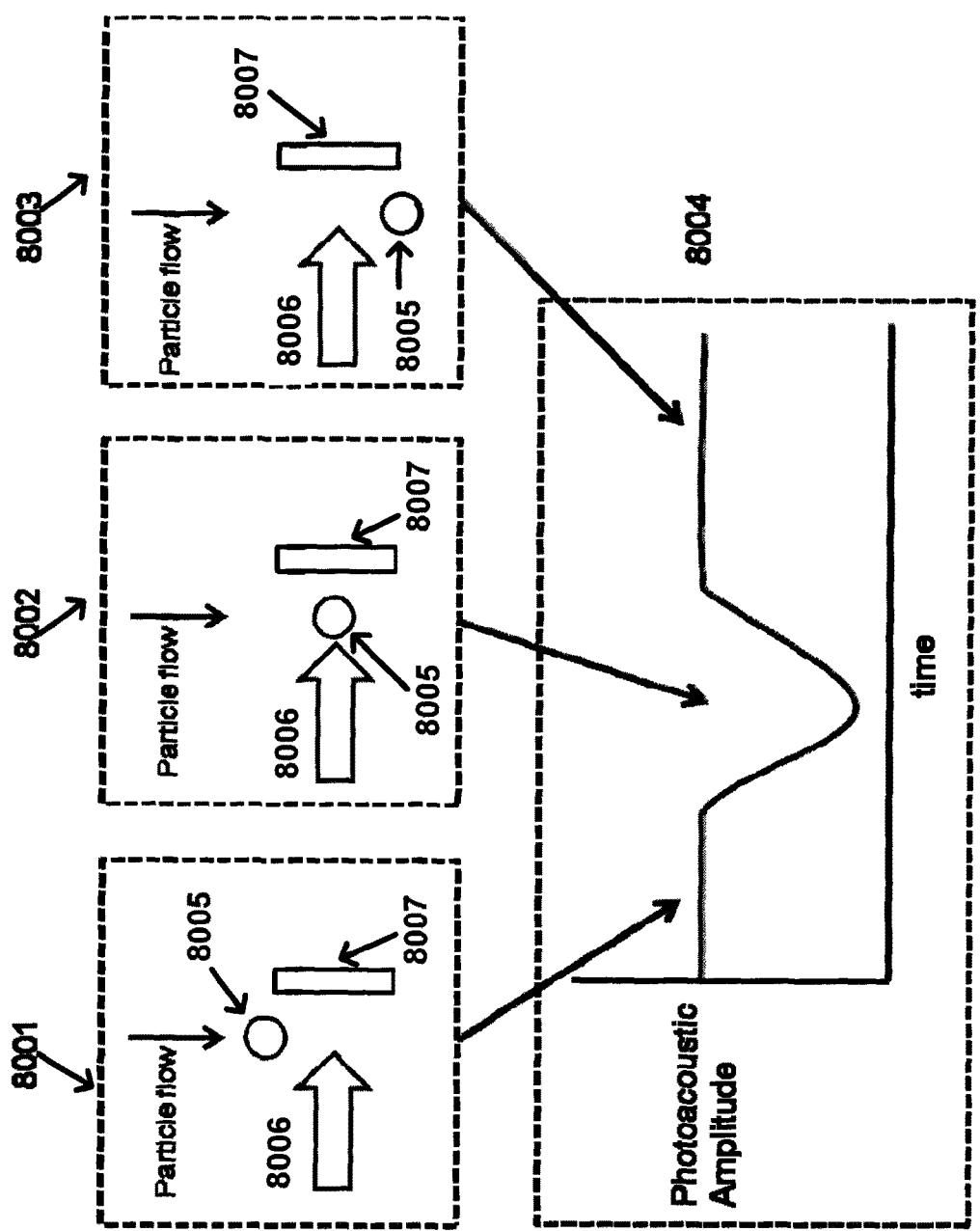
FIG. 8 depicts an overview of a photoacoustic extinction method to measure a change in photoacoustic signal at the transducer as a particle passes through the laser light, according to non-limiting implementations.

In general, the size of a moving particle can be measured from the photoacoustic extinction signal as it passes through an ultrasound pulse or laser beam, and can be used to improve the accuracy of the described PA/US spectral analysis and/or transmission ultrasound calculations as illustrated by FIG. 8 in which boxes 8001, 8002, 8003 and 8004 are depicted.

Figure 9:
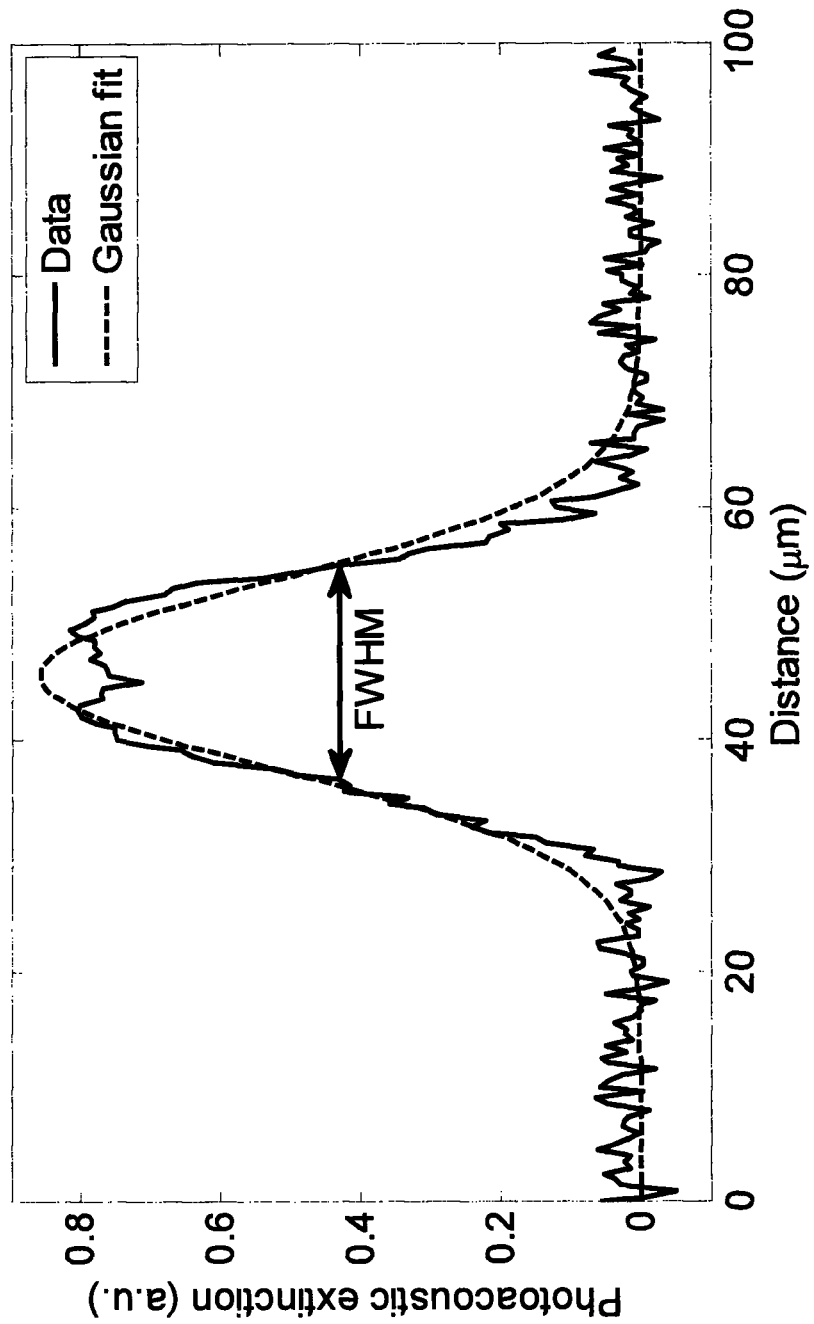
FIG. 9 depicts a photoacoustic extinction signal of a 20 µm polystyrene bead passing through a laser light, according to a non-limiting implementation. In this implementation, the particle diameter is equal to the full width half maximum (FWHM).

As illustrated by box 8001 in FIG. 8, in the absence of particle 8005, laser light 8006 hits ultrasound transducer 8007 opposite laser light 8006 and a photoacoustic pressure wave internal to transducer 8007 is created. The amplitude of the signal, as illustrated by box 8004, is proportional to the intensity of laser light 8006. As particle 8005 moves past laser light 8006, as illustrated by box 8002, it obstructs laser light 8006 and the intensity of laser light 8006 hitting ultrasound transducer 8007 decreases. As particle 8005 clears the path of laser light 8006, the intensity of laser light 8006 hitting ultrasound transducer 8007 increases, and the photoacoustic signal amplitude increases (illustrated by box 8003). Plotting the photoacoustic signal amplitude vs. time, as illustrated by box 8004, shows a drop in the photoacoustic signal as particle 8005 passes in front of laser light 8006. The photoacoustic extinction signal can then be calculated by inverting and normalizing the photoacoustic signal, and converting the time to distance using the known flow velocity, as shown in FIG. 9, where the photoacoustic extinction signal was used to determine the diameter of a solid polystyrene micro-bead particle 20 µm in diameter. The full width half maximum (FWHM) of the photoacoustic extinction signal vs. distance plot gives the particle diameter. The same methodology could be used to determine particle size moving through an ultrasound pulse (or beam) when the ultrasound transducers are opposite each other.

The measurement of biological cells is one application of the described PA/US spectral methods and systems. In general, good agreement was found between the measured photoacoustic power spectrum from cells and theory, where various optical absorbing agents such as melanin (endogenous to melanocyte cells) and common inexpensive stains (such as trypan blue) were used to induce a photoacoustic wave. In some implementations, other optical absorbing agents, such as nanoparticles, beads or molecular agents could also be used provided they absorb light to induce a photoacoustic wave from the particle. The PA/US spectral minima and maxima occur at different locations due to differences in a particle shape, morphology and composition. In addition, the photoacoustic spectral amplitude is a measure of the optical absorbing properties and thermal properties of the particle. This enables a better determination of the particle size, shape and morphology than using either ultrasound or photoacoustics alone. When combined with the photoacoustic extinction signal measurement to determine the cell diameter, the diameter can be fixed for a more accurate determination of the other parameters.

Attention is next directed to FIG. 10, in which an unstained B16 melanoma cell (depicted in the top left-hand corner of FIG. 10) was measured according to an implementation of the described PA/US spectral methods and systems. In this example cell, the melanin is distributed throughout the cytoplasm only, and does not occur within the nucleus. This creates a ring of optical absorbing particles surrounding the nucleus, and therefore the photoacoustic pressure wave is generated from the ring, but not the nucleus. In this case, the analytical solution, shown in equation (1), may not be valid. Therefore a FEM was used to calculate the photoacoustic pressure wave from the cell, where the cell diameter and nucleus were determined from optical measurements. Multiphysics FEM software (from COMSOL AB of Stockholm Sweden) was used to solve the FEM. Within the FEM, the pressure of the optical absorbing areas was set to unity, and all other areas were set to zero. A transient acoustic model calculated the acoustic wave propagation due to the pressure differential within the model. For the ultrasound aspect, the Anderson model, shown in equation (2), was used to calculate the backscattered ultrasound wave. Using the measured diameter as a constant, the parameters in the FEM were adjusted until a fit between measured and theory was found.

Next, attention is directed to FIG. 11, in which an example MCF7 cell stained with trypan blue (depicted in the top left-hand corner of FIG. 11) was measured according to an implementation of the described PA/US spectral methods and systems. Trypan blue is an inexpensive dye commonly used to visually identify viability which has a broad optical absorption peak from about 500 to nearly 700 nm. Trypan blue penetrates the cell membranes of non-viable cells, but not viable cells. Typically, no fluorescence is required using the described PA/US spectral methods and systems, in contrast to expensive reagents commonly used in flow cytometry (e.g. propidium iodide). In this implementation, the model parameters in the photoacoustic and ultrasound backscatter models were adjusted until good agreement between theory and the measured spectra were observed. Trypan blue was used to show that the described PA/US spectral methods and systems could be used with common inexpensive stains; other stains or colorimetric assays, such as methyl blue, neutral red, crystal violet, MTT 9 (3-(4,5-Dimethylthiazol-2-yl)-2,5-diphenyltetrazolium bromide), and indocyanine green could also be used provided they are irradiated at an appropriate wavelength.

Next, attention is directed to FIG. 12, in which a 2.45 µm liquid PFC emulsion containing optically absorbing nanoparticles was measured according to an implementation of the described photoacoustics methods and systems. The location of the photoacoustic spectral minima and maxima agree well with theory.

Next, attention is directed to FIG. 13, in which RBCs were measured according to an implementation of the described photoacoustics methods and systems. The RBC was oriented so that the long edge was towards the ultrasound transducer. The photoacoustic power spectrum can be used to determine the size, orientation and morphology of RBCs. Typically, no analytical solution of the photoacoustic pressure wave emitted from RBCs exists due to their unique biconcave shape. A FEM was developed in the same manner as previously discussed with the melanoma cells. The pressure within the RBC was set to unity, and the pressure set to zero in all other areas. The diameter and orientation of the immobilized RBCs were determined to be 8 μm optically, then the photoacoustic power spectrum was measured from those cells using a 375 MHz ultrasound transducer. These measurements were then compared to theoretical results. Good agreement in the location of the spectral minima and maxima was observed between theory and measured over the bandwidth of the ultrasound transducer (approximately 150 to 500 MHz), thus validating the described photoacoustic methods and systems to determine the size and orientation of single RBCs.

Graphing particle characterization data, acquired by any appropriate method, can be used as a visual aid to help identify and differentiate cell populations within a sample particle or particles. However, it is appreciated that such graphs need not be specifically produced, and that particles can be identified by comparing acquired particle characterization data with reference power spectra using processing unit 3012, for example, and outputting an identifier of the particle(s) based thereupon.

In fluorescence flow cytometry, the presence or absence of a stain in a cell is used to identify cell populations and types within a sample particle or particles. For example, Annexin-V (fluoresces green) and propidium iodide (fluoresces red) are frequently used to detect apoptosis (cell death) in cancer cells. The relative intensities of each stain are graphed, and cell populations are observed in each quadrant (AV+/−, PI+/−).

Similar graphs can be derived using the described PA/US methods and systems to determine cell/particle populations using acoustic and/or photoacoustic pressure waves (indicated by the respective acoustic and photoacoustic pressure signals), or cell properties determined from the described PA/US spectral methods and systems. In another example implementation, properties of cells in various states (interphase, early/late stage apoptosis, mitosis) and different cell types (benign vs. malignant) were calculated using acoustic microscopy methods. FIG. 14 plots the sound speed vs. cell diameter to differentiate early, late stage apoptosis and the metaphase stage of mitosis using parameters that could be obtained from the described PA/US spectral methods and systems. While data for these example implementations were found using acoustic microscopy methods, the same properties could be determined using the described PA/US methods and systems. In another example implementation, combining the PA/US spectral results with transmission ultrasound results can add additional parameters to differentiate cell populations. For example, FIG. 15 plots the sound speed vs. acoustic impedance to differentiate early and late stage apoptosis, and FIG. 16 plots the attenuation vs. diameter to differentiate malignant and benign cells. These graphs are not limited to cell populations; they could also be used with other types of particles, such as emulsions and solid particles to show size/parameter variations within a sample. The US and/or PA signals can be used instead of the spectrum for particle detection. As particles flow through the target area, the presence of an US signal determines if a particle is present, and the presence/absence of a PA signal determines if an internal/external optically absorbing additive (such as a stain, nanoparticle, etc.) is present. In this way, cell counts can be performed. For example, to probe cell viability, a stain is added to the sample (such as trypan blue, propidium iodide, etc.). By counting the number of cells present (via US) and number of stained cells (via PA), a count of cells containing the dye can be completed. Using one method of US or PA alone may not be sufficient to determine an accurate cell count. As stated above, this technique is not limited to using US and PA only; many detection methods could be used, such as fluorescence, light scattering, electrical impedance, optical absorption/transmission and the above-described PA extinction method.

Applications:

The photoacoustic and ultrasound spectra as a function of light wavelength can also be used for particle identification. An example application of the described PA/US methods and systems is examining the oxygenation content of RBCs. It is known that the optical absorption of RBCs varies with oxygenation. At 700 nm, the optical absorption of deoxygenated blood is several times larger than oxygenated blood, while at 1000 nm, the opposite is true. The photoacoustic spectral amplitude is directly related to the optical absorption; by comparing the photoacoustic amplitude vs. irradiating wavelength, the oxygenation (as well as other RBC properties) could be determined using the described PA/US spectral methods and systems. The described PA/US spectral methods and systems are not restricted to RBCs; it can be used for any particle where there is a change in absorption as a function of wavelength. This may be due to the inherent changes in absorption with wavelength, or, it may be due to a physiological parameter that changes the absorption (such as oxygenation). RBCs can aggregate under certain situations (such as anemia) and form spherical or cylindrical (rouleaux) aggregates up to several hundred micrometers in size. The photoacoustic and ultrasonic power spectrum is known to vary from about 10 to 1000 MHz, depending on the size of the aggregate; the amount of aggregation could be determined using the described PA/US spectral method and system.

High frequencies (over 100 MHz) can be challenging to use in-vivo and/or non-invasively due to the high attenuation that occurs in tissue. However high frequency probes up to 100 MHz could potentially be applied to the skin surface to examine sub-surface capillaries and arteries. The bandwidth of the ultrasound transducers under 100 MHz may be insufficient to compare the spectral features directly to theory; however, the amplitude and shape of the spectrum up to 100 MHz using quantitative ultrasound methods (slope, mid-band fit and y-intercept or other methods) could be compared. At these frequencies, the ultrasound backscatter and/or photoacoustic waves from the capillary could be detected and used for particle detection in-vivo.

A complete blood count (CBC) could be performed, where RBCs, white blood cells (WBCs), platelets and foreign cells within a blood sample are identified using label-free methods. The size and shape of each cell could be identified through the spectral features, and the hemoglobin determined from the RBC signal amplitude. These measurements could also be used to identify blood-related disease, infection or malignancies, and/or circulating tumor cells within the blood. In some cases, the PA/US pressure waves, as indicated by the respective PA and US pressure signals, could be used to count and differentiate RBCs from WBCs (due to the inherent absorption of light by RBCs, but lack of absorption by WBCs). Adding stains would further increase the specificity, allowing for determination of cell sub-populations. This could be a significant advancement over current hematology analyzers, which generally require multiple channels and lysing agents to perform a blood count.

Another potential application of the described PA/US spectral methods and systems is the integration of the ultrasound transducers into current flow cytometry and/or particle sorting systems. For example, sorters also use various parameters to sort particles into collection tubes for later analysis. In addition to the current flow cytometry method (light scattering, optical imaging, fluorescence or electrical impedance), the ultrasound transducers can be positioned around the flowing particles to detect the photoacoustic waves and ultrasound backscatter. In some implementations, the existing laser could be configured for photoacoustic measurements.

Typically, more information can be obtained from the combined PA/US methods and systems than any other system alone; the described PA/US methods and systems could be used to increase particle detection accuracy over the current flow cytometry systems, in addition to adding valuable information that current flow cytometers cannot give (such as particle composition).

In the above example implementations, focused ultrasound transducers were used which require the ultrasound transducers and laser (if focused) to be focused at the same spot, and the particles to be situated at that spot. In some implementations, unfocused ultrasound transducers can be used as receivers during photoacoustic and ultrasound measurements. Unfocused ultrasound transducers have reduced signal-to-noise ratios (SNR), but do not have to be positioned as accurately as focused transducers. Moreover, unfocused ultrasound transducers can be positioned very close to the particle to reduce attenuation losses.

Furthermore, particles are known to emit a unique photoacoustic signal upon ablation. This signal is different than what is normally recorded below the ablation threshold. In this implementation, the laser intensity is increased to cause explosive rupturing of the particle, where the photoacoustic signal is recorded.

Attention is now directed to FIG. 17 which depicts a flowchart of a method 1700 for detecting and classifying a particle (or particles), according to non-limiting implementations. The particle or particles can comprise one or more of a solid particle, a solid spherical particle, a liquid particle and a liquid spherical particle. In order to assist in the explanation of method 1700, it will be assumed that method 1700 is performed using system 3000. Furthermore, the following discussion of method 1700 will lead to a further understanding of system 3000 and its various components. However, it is to be understood that system 3000 and/or method 1700 can be varied, and need not work exactly as discussed herein in conjunction with each other, and that such variations are within the scope of present implementations.

It is appreciated that, in some implementations, method 1700 is implemented in system 3000 by processing unit 3012 of computing device 3011. Indeed, method 1700 is one way in which computing device 3011 can be configured. It is to be emphasized, however, that method 1700 need not be performed in the exact sequence as shown, unless otherwise indicated; and likewise various blocks may be performed in parallel rather than in sequence; hence the elements of method 1700 are referred to herein as "blocks" rather than "steps". It is also to be understood, however, that method 1700 can be implemented on variations of system 3000 as well. For example, method 1700 could employ one, two, three or more ultrasound transducers.

At block 1710, light source 3001 and ultrasound transducers 3003-3005 are controlled to irradiate particle 3002 with light and an ultrasound pulse. In some implementations, only light source 3001 is employed to irradiate particle 3002. In some implementations, only one or more of ultrasound transducers 3003-3005 is employed to irradiate particle 3002. In some implementations, both light source 3001 and at least one of ultrasound transducers 3003-3005 are employed to irradiate particle 3002. In some implementations, light source 3001 comprises a laser, which, in a non-limiting example, could comprise a pulsed laser. It is understood that the term "irradiate" comprises any suitable mode of exposing particle 3002 to radiation, including by, but not limited to, electromagnetic radiation such as light, microwaves, radio waves, heat and ultrasound.

In some implementations, the ultrasound pulse is in a range of about 100 MHz to about 1000 MHz. In some implementations, the ultrasound pulse is in a range up to about 1000 MHz, including, but not limited to a range of about 100 MHz to about 1000 MHz. For example, the ultrasound pulse could be in a range of about 10 MHz up to about 1000 MHz.

In some implementations, controlling one or more of light source 3001 and ultrasound transducers 3003-3005 to irradiate particle 3002 comprises alternately irradiating the particle with one of the light and the ultrasound pulse and then the other of the light and the ultrasound pulse.

At block 1720, a feature associated with particle 3002 is determined by processing ultrasound data resulting from particle 3002 being irradiated. In some implementations, one or more of ultrasound transducers 3003-3005 is configured to measure one or more of a photoacoustic wave and a pressure wave resulting from the irradiation of particle 3002 by the light and the ultrasound pulse. In some implementations, the ultrasound data comprises data received from one or more of ultrasound transducers 3003-3005 when the one or more of ultrasound transducers 3003-3005 is measuring the photoacoustic wave and/or pressure wave. In some implementations, the feature comprises one or more of an amplitude and an intensity of a pressure wave received by one or more of ultrasound transducers 3003-3005. In some implementation, the feature comprises a power spectrum of the particle. In some implementations, the ultrasound data comprises data resulting from detecting one or more of a photoacoustic pulse and an ultrasound pulse.

For example, at block 1730, a power spectrum of particle 3002 is determined by processing ultrasound data resulting from particle 3002 being irradiated. In some implementations, ultrasound data comprises any information suitable for system 3000 or similar system to determine a power spectrum of particle 3002 after or while particle 3002 is being irradiated. In some implementations, the ultrasound data is indicative of one or more of an ultrasound wave and a scattered ultrasound wave produced when the particle is irradiated. In some implementations, ultrasound data comprises at least one signal, such as photoacoustic signal and/or ultrasonic signal.

In some implementations, the ultrasound data is received from at least one ultrasound transducer, which in turn measures a received ultrasound pulse from particle 3002 and converts the received ultrasound pulse into the ultrasound data. In related implementations, the at least one of ultrasound transducer comprises one or more of ultrasound transducers 3003-3005 and a further ultrasound transducer.

As a non-limiting example, when block 1710 is performed using a single light source and a single ultrasound transducer, according to some implementations, the ultrasound transducer could be employed to irradiate particle 3002 and a further ultrasound ultrasound transducer could be employed to receive the ultrasound pulse and convert the received ultrasound pulse to the ultrasound data. Likewise, in some implementations, when block 1710 is performed using one or more light sources and more than one ultrasound transducer, at least a further ultrasound transducer could be employed to receive the ultrasound pulse and convert the received ultrasound pulse to the ultrasound data. In some implementations, at least one of the ultrasound transducers employed to irradiate particle 3002 is also employed to receive the ultrasound pulse and convert the received ultrasound pulse to the ultrasound data. Other combinations of ultrasound transducers employed to irradiate particle 3002 and/or receive the ultrasound pulse and convert the received ultrasound pulse to the ultrasound data will occur to persons skilled in the art and are within the scope of present implementations.

In some implementations, the power spectrum is determined by applying a Fast Fourier Transform (FFT) to the ultrasound data. It is understood that any suitable technique for determining the power spectrum of particle 3002 while or after particle 3002 has been irradiated are within the scope of present implementations.

At block 1740, the determined power spectrum of particle 3002 is compared to a reference power spectrum. In some implementations, the reference power spectrum comprises one or more of a control power spectrum and a theoretical model power spectrum. In some implementation, the control power spectrum comprises a power spectrum derived from a sample particle having known properties. In some implementation, the theoretical model power spectrum can be based upon one or more of an ultrasound scattering model, photoacoustic generation model or a finite element model (FEM). As a non-limiting example, the theoretical model power spectrum can comprise one or more of a Diebold model, Anderson model and/or a Faran model. It is understood that the reference power spectrum comprises any known or theoretical model power spectrum suitable for comparison with the power spectrum of particle 3002 after particle has been irradiated.

At block 1750, at least one property of particle 3002 is determined based on the comparison between the determined power spectrum and the reference power spectrum. As a non-limiting example, the determined property or properties could comprise one or more of the size, orientation, morphology, composition, sound speed, density and elasticity of particle 3002.

As another example, at block 1760 one or more of an amplitude and an intensity of a pressure wave received by one or more of ultrasound transducers 3003-3005 is determined based on the processing of ultrasound data at block 1720. In some implementations, ultrasound data comprises any information suitable for system 3000 or similar system to determine an amplitude and an intensity of a pressure wave received by one or more of ultrasound transducers 3003-3005, and emitted by particle 3002, after or while particle 3002 is being irradiated. In some implementations, light-based analysis techniques to assist in determining the feature of particle 3002. For example, one or more of photoacoustics, fluorescence, light scattering, light transmission and absorbance can be used to assist in determining the feature of the particle 3002.

At block 1770, the determined amplitude and/or intensity is compared to a reference, such as a reference data set or a control sample.

At block 1780, at least one property of particle 3002 is determined based on the comparison performed at block 1770. For example, one or more of a type (e.g. such as a cell type), a count and a state (e.g. such as whether particle 3002 is a live cell or a dead cell) of particle 3002.

In some implementations, the ultrasound data is processed to determine features or characteristics in a range of about 100 MHz to about 1000 MHz of the power spectrum. In some implementations, the ultrasound data is processed to determine features or characteristics in a range up to about 1000 MHz, including, but not limited to a range of about 100 MHz to about 1000 MHz. For example, the ultrasound data could be processed to determine features or characteristics in a range of about 10 MHz up to about 1000 MHz.

Those skilled in the art will appreciate that in some implementations, the functionality of system 3000 and/or computing device 3011 can be implemented using pre-programmed hardware or firmware elements (e.g., application specific integrated circuits (ASICs), electrically erasable programmable read-only memories (EEPROMs), etc.), or other related components. In other implementations, the functionality of system 3000 and/or computing device 3011 can be achieved using a computing apparatus that has access to a code memory (not shown) which stores computer-readable program code for operation of the computing apparatus. The computer-readable program code could be stored on a computer readable storage medium which is fixed, tangible and readable directly by these components, (e.g., removable diskette, CD-ROM, ROM, fixed disk, USB drive). Furthermore, it is appreciated that the computer-readable program can be stored as a computer program product comprising a computer usable medium. Further, a persistent storage device can comprise the computer readable program code. It is yet further appreciated that the computer-readable program code and/or computer usable medium can comprise a non-transitory computer-readable program code and/or non-transitory computer usable medium. Alternatively, the computer-readable program code could be stored remotely but transmittable to these components via a modem or other interface device connected to a network (including, without limitation, the Internet) over a transmission medium. The transmission medium can be either a non-mobile medium (e.g., optical and/or digital and/or analog communications lines) or a mobile medium (e.g., microwave, infrared, free-space optical or other transmission schemes) or a combination thereof.

Persons skilled in the art will appreciate that there are yet more alternative implementations and modifications possible, and that the above examples are only illustrations of one or more implementations. The scope, therefore, is only to be limited by the claims appended hereto.

What is claimed is:

1. A method to detect, characterize and classify a particle comprising:

controlling a light source and at least one ultrasound transducer to irradiate the particle with light and an ultrasound pulse one of simultaneously and sequentially, the ultrasound pulse being in a range of about 100 MHz to about 1000 MHz;

determining a characteristics of a power spectrum associated with the particle by processing ultrasound data resulting from the particle being irradiated, the ultrasound data comprising data resulting from detecting a photoacoustic pulse generated by irradiating the particle with the light and a second ultrasound pulse generated by irradiating the particle with the ultrasound pulse, the characteristics of the power spectrum determined over a range located within about 100 MHz to about 1000 MHz of the power spectrum; and comparing the characteristics of a power spectrum to a reference power spectrum to determine at least one property of the particle.

2. The method of claim 1, further comprising: determining one or more of an amplitude and an intensity of a pressure wave received by the at least one ultrasound transducer over the range; and using one or more of the amplitude and the intensity over the range to further determine the at least one property of the particle.

3. The method of claim 2, wherein the at least one property comprises one or more of a type, a count and a state of the particle.

4. The method of claim 1, further comprising using a light-based analysis technique to assist in determining the power spectrum of the particle.

5. The method of claim 4, wherein the light-based analysis technique comprises one or more of photoacoustics, fluorescence, light scattering, spatially localized light scattering, light transmission and absorbance.

6. The method of claim 1, wherein the at least one ultrasound transducer is configured to measure one or more of a photoacoustic wave and a pressure wave resulting from irradiation of the particle by the light and the ultrasound pulse.

7. The method of claim 6, wherein the ultrasound data comprises data received from the at least one ultrasound transducer when the at least one ultrasound transducer is measuring the one or more of a photoacoustic wave and a pressure wave.

8. The method of claim 1, wherein the reference power spectrum comprises one or more of a control power spectrum and a theoretical model power spectrum.

9. The method of claim 8, wherein the theoretical model power spectrum is based on one or more of an ultrasound scattering model, photoacoustic generation model or a finite element model.

10. The method of claim 1, wherein the determining the power spectrum comprises applying a Fast Fourier Transform (FTT) to the ultrasound data.

11. The method of claim 1, wherein the ultrasound data is received from the at least one ultrasound transducer which measures a received ultrasound pulse from the particle and converts the received ultrasound pulse to the ultrasound data.

12. The method of claim 1, wherein the ultrasound data is indicative of one or more of an ultrasound wave and a scattered ultrasound wave produced when the particle is irradiated.

13. The method of claim 1, wherein controlling the light source and the at least one ultrasound transducer to irradiate the particle comprises alternately irradiating the particle with one of the light and the ultrasound pulse and then the other of the light and the ultrasound pulse.

14. The method of claim 1, wherein the particle comprises one or more of a solid particle, a solid spherical particle, a liquid particle, a liquid spherical particle and a gas particle.

15. The method of claim 1, wherein the at least one property comprises one or more of a size, an orientation, a morphology and a composition of the particle.

16. The method of claim 1, wherein the light source comprises a laser.

17. A computing device to detect, characterize and classify a particle, comprising:
a processing unit and a memory device, the processing unit enabled to:
receive the input data and control a light source and at least one ultrasound transducer to irradiate the particle with light and an ultrasound pulse one of simultaneously and sequentially based on the input data, the ultrasound pulse being in a range of about 100 MHz to about 1000 MHz;
determine a characteristics of a power spectrum associated with the particle by processing ultrasound data resulting from the particle being irradiated, the ultrasound data comprising data resulting from detecting a photoacoustic pulse generated by irradiating the particle with the light and a second ultrasound pulse generated by irradiating the particle with the ultrasound pulse, the characteristics of the power spectrum determined over a range located within about 100 MHz to about 1000 MHz of the power spectrum, and
compare the characteristics of a power spectrum to a reference power spectrum to determine at least one property of the particle.

18. The computing device of claim 17, wherein the processing unit is further enabled to: determine one or more of an amplitude and an intensity of a pressure wave received by the at least one ultrasound transducer over the range; and use one or more of the amplitude and the intensity over the range to further determine the at least one property of the particle.

19. The computing device of claim 17, wherein the at least one ultrasound transducer is configured to measure one or more of a photoacoustic wave and a pressure wave resulting from irradiation of the particle by the light and the ultrasound pulse.

20. The computing device of claim 19, wherein the ultrasound data comprises data received from the at least one ultrasound transducer when the at least one ultrasound transducer is measuring the one or more of a photoacoustic wave and a pressure wave.

21. The computing device of claim 17, wherein the determination of the power spectrum comprises applying a Fast Fourier Transform (FTT) to the ultrasound data.

22. The computing device of claim 17, wherein the ultrasound data is received from the least one ultrasound transducer which measures a received ultrasound pulse from the particle and converts the received ultrasound pulse to the ultrasound data.

23. The computing device of claim 17, wherein control of the light source and the at least one ultrasound transducer to irradiate the particle comprises alternately irradiating the particle with one of the light and the ultrasound pulse and then the other of the light and the ultrasound pulse.

24. The computing device of claim 17, wherein the light source comprises a laser.

* * * * *